(12) United States Patent
Avrameas

(10) Patent No.: US 7,544,664 B2
(45) Date of Patent: Jun. 9, 2009

(54) SEQUENCES FACILITATING PENETRATION OF A SUBSTANCE OF INTEREST

(75) Inventor: Alexandre Avrameas, Chatellerault (FR)

(73) Assignee: Diatos, S.A., Paris (FR)

( * ) Notice: Subject to any disclaimer, the term of this patent is extended or adjusted under 35 U.S.C. 154(b) by 9 days.

(21) Appl. No.: 10/568,108

(22) PCT Filed: Aug. 13, 2004

(86) PCT No.: PCT/IB2004/002936

§ 371 (c)(1),
(2), (4) Date: Feb. 13, 2006

(87) PCT Pub. No.: WO2005/016960

PCT Pub. Date: Feb. 24, 2005

(65) Prior Publication Data

US 2007/0042492 A1 Feb. 22, 2007

(30) Foreign Application Priority Data

Aug. 14, 2003 (EP) .................. 03292030
Aug. 14, 2003 (FR) .................. 03 09962

(51) Int. Cl.
| | |
|---|---|
| A61K 38/00 | (2006.01) |
| A61K 38/10 | (2006.01) |
| A61K 38/16 | (2006.01) |
| C07K 7/00 | (2006.01) |
| C07K 7/04 | (2006.01) |
| C07K 7/08 | (2006.01) |
| C07K 14/00 | (2006.01) |

(52) U.S. Cl. .................. 514/13; 514/2; 530/300; 530/326

(58) Field of Classification Search .................. None
See application file for complete search history.

(56) References Cited

U.S. PATENT DOCUMENTS

| | | | |
|---|---|---|---|
| 3,710,795 | A | 1/1973 | Higuchi et al. |
| 4,526,888 | A | 7/1985 | Williams et al. |
| 5,262,564 | A | 11/1993 | Kun et al. |
| 5,521,291 | A | 5/1996 | Curiel et al. |
| 5,547,929 | A | 8/1996 | Anderson et al. |
| 5,624,894 | A | 4/1997 | Bodor |
| 5,635,383 | A | 6/1997 | Wu et al. |
| 6,043,339 | A | 3/2000 | Lin et al. |
| 6,066,485 | A | 5/2000 | Guthridge et al. |
| 6,274,712 | B1 | 8/2001 | Springer et al. |
| 6,750,321 | B1 | 6/2004 | Chen et al. |
| 6,835,536 | B2 | 12/2004 | Krieger et al. |
| 6,855,801 | B1 | 2/2005 | San Antonio et al. |
| 7,049,286 | B2 | 5/2006 | Tchelingerian |
| 7,112,562 | B2 | 9/2006 | Tchelingerian |
| 2003/0153490 | A1 | 8/2003 | Tchelingerian |
| 2003/0199677 | A1 | 10/2003 | Avrameas et al. |
| 2004/0123343 | A1* | 6/2004 | La Rosa et al. .............. 800/278 |
| 2006/0281897 | A1 | 12/2006 | Trouet et al. |
| 2007/0042492 | A1 | 2/2007 | Avrameas |
| 2007/0259813 | A1* | 11/2007 | Arranz .................. 514/12 |

FOREIGN PATENT DOCUMENTS

| | | |
|---|---|---|
| WO | WO 90/12587 | 11/1990 |
| WO | WO 91/04315 | 4/1991 |
| WO | WO 94/28921 | 12/1994 |
| WO | WO 96/06632 | 3/1996 |
| WO | WO 96/08274 | 3/1996 |
| WO | WO 96/38163 | 12/1996 |
| WO | WO 97/02840 | 1/1997 |
| WO | WO 98/40401 | 9/1998 |
| WO | WO 98/56938 | 12/1998 |
| WO | WO 99/06632 | 2/1999 |
| WO | WO 99/07414 | 2/1999 |
| WO | WO 99/32136 | 7/1999 |
| WO | WO 99/67284 | 12/1999 |
| WO | WO 00/45831 | 8/2000 |
| WO | WO 01/64738 | 9/2001 |
| WO | WO 03/018636 | 3/2003 |
| WO | WO 03/092736 | 11/2003 |

(Continued)

OTHER PUBLICATIONS

Seq ID No. 178781 from PG Pub 2004/0123343.*
Avrameas, "Efficient Gene Delivery by a Peptide Derived from a Monoclonal anti-DNA Antibody," Bioconjugate Chem., 1999, 10, pp. 87-93.
Bernfield, "Biology of the syndecans: a family of transmembrane heparan sulfate proteoglycans," Annu. Rev. Cell Biol., 8:365-393 (1992).

(Continued)

Primary Examiner—Cecilia Tsang
Assistant Examiner—Julie Ha
(74) Attorney, Agent, or Firm—Hunton & Williams LLP

(57) ABSTRACT

The present invention relates to an amino acid sequence being able to facilitate penetration of a substance of interest inside cells and/or cell nuclei and having the following formula (I) $[(X_1)_p [(X)_o (B)_n X B X X B]_m (X_2)_q$ wherein $X_1$ and $X_2$ are amino acid sequences of 1 to 20 amino acids; p and q are whole numbers between 0 and 5; B is a basic amino acid; X is a non-basic, preferably hydrophobic amino acid, such as alanine, isoleucine, leucine, methionine, phenylalanine, tryptophan, valine or tyrosine; n is 2 or 3; m is 1 to 4; o is 0 or 1, between 0 and 5; B is a basic amino acid; X is a non-basic, preferably hydrophobic amino acid, such as alanine, isoleucine, leucine, methionine phenylalanine, tryptophan, valine or tyrosine; n is 2 or 3; m is 1 to 4; o is 0 or 1.

4 Claims, 18 Drawing Sheets

FOREIGN PATENT DOCUMENTS

| WO | WO 03/106491 | 12/2003 |
|---|---|---|
| WO | WO 2004/011033 | 2/2004 |
| WO | WO 2005/016960 | 2/2005 |

OTHER PUBLICATIONS

Bosanquet, "Chlorambucil: stability of solutions during preparation and storage," Cancer Chemother. Pharmacol., 18:176 (1986).
Cardin, "Molecular modeling of protein-glycosaminoglycan interactions," Arterioscler. Thromb. Vasc. Biol. 1989; 9; pp. 21-32.
Darveau, "Beta-Lactam Antibiotics potentiate Magainin 2 Antimicrobial Activity In Vitro and In Vivo," Antimicrobial Agents and Chemotherapy, American Society for Microbiology, vol. 35, No. 6, 1991, pp. 1153-1159.
David, "Integral membrane heparan sulfate proteoglycans," 7:1023, 1993.
Esko, "Animal cell mutant in glycosaminoglycan biosynthesis," Proc. Natl. Acad. Sci., vol. 82, pp. 3197-3201, 1985.
Gueritte, "Relationships between the Structure of Taxol Analogues and Their Atnimitotic Activity," J. Med. Chem., 34, 1991, pp. 992-996.
Morrow, "Coordinated Action of Glutathione S-Transferases (GSTs) and Multidrug Resistance Protein 1 (MRP1) in Antineoplastic Drug Detoxification," J. Biol. Chem., vol. 273, No. 32, pp. 20114-20120, 1998.
Niidome, "Chain Length of Cationic alpha-Helical Peptide Sufficient for Gene Delivery into Cells," Bioconjugate Chemistry, vol. 10, No. 5, 1999, pp. 773-780.
Nogales, "A structure view of microtubule dynamics," Cell. Mol. Life Sci., vol. 56, 1999, pp. 133-142.
Park, "Mechanism of Action of the Antimicrobial Peptide Buforin II: Buforin II Kills Microorganisms by Penetrating the Cell Membrane and Inhibiting Cellular Functions," Biochem. Biophys. Res. Commun., 244, pp. 253-257, 1998.
Rostand, "Microbial Adherence to and Invasion Through Proteoglycans," Infection and Immunity, pp. 1-8, 1997.
Silber, "Chemosensitivity of Lymphocytes From Patients With B-Cell Chronic Lymphocytic Leukemia to Chlorambucil Fludarabine, and Camptothecin Analogs," Blood, 84:3440, 1994.
Tabosa, "In-vitro and In-vivo evaluation of a new amphotericin B emulsion-based delivery sysytem," J. Antimicrob. Vhemother., 38, pp. 485-497, 1996.
Travis, "Risk of Leukemia Following Treatment for Non-Hodgkin's Lymphoma," J. Natl. Cancer Inst., 86:1450, 1994.
Wall, "Camptothecin and Taxol: Discovery to Clinic—Thirteenth Bruce F. Cain Memorial Award Lecture," Cancer Res., 55:753, 1995.
Zunino, "Molecular mechanisms of resistance to taxanes and therapeutic implications," Drug Resist. Updat., 2:351, 1999.
International Search Report for International Application No. PCT/IB2004/002936. mailed Oct. 2, 2005.
French Search Report for French Patent Application No. FR0309962 mailed Mar. 10, 2004.
Partial European Search Report for European Patent Application No. EP 03292030 mailed Mar. 1, 2004.
Written Opinion for International Application No. PCT/IB2004/002936.
International Preliminary Report on Patentability for International Application No. PCT/IB2004/002936, issued Feb. 21, 2006.
Accession No. 600165A (Jul. 10, 1992) Insulin.
Accession No. 550085A (Jul. 10, 1992) Insulin.
Accession No. AAH05255 (Jun. 23, 2006) Insulin [*Homo sapiens*].
Accession No. AAA59179 (Jan. 6, 1995) Insulin [*Homo sapiens*].
Accession No. AAW99570 (Feb. 14, 2005) Sequence 35 from U.S. Patent No. 6,835,536.
Amara, et al. (1999) Journal of Biological Chemistry 274: 23916-23925.
Arkonac, et al. (1998) Journal of Biological Chemistry 273: 4400-4405.
Avrameas, et al. (1998) Proc. Natl. Acad. Sci. 95: 5601-5606.
Caldwell, et al. (1996) Int. J. Biochem. Cell Biol. 28: 203-216.
Campanelli, et al. (1996) Development 122: 1663-1672.
Cardin, et al. (1988) Biochem. Biophys. Res. Com. 154: 741-745.
Castellot, et al. (May 1986) J. Cell Biol. 102: 1979-1984.
Dini, et al. (1996) Cellular and Molecular Biology 42(2): 269-277.
Fowlkes, et al. (1997) Endocrinol 138: 2280-2285.
Fromm, et al. (1997) Arch. Biochem. Biophys. 343(1): 92-100.
Grieb, et al. (1998) Biochem. Biophys. Res. Comm. 246: 182-191.
Guevara, et al. (1999) Journal of Protein Chemistry 18(8): 845-857.
Hasan, et al. (1999) J. Immunol. 162: 1064-1070.
Hirabayashi, et al. (1993) Scand. J. Immunol. 37: 533-540.
Hirsch (1991) New Engl. J. Med. 324:1565.
Inoue, et al. (1990) FEBS 269: 89-92.
Javadpour, et al. (1996) J. Med. Chem. 39: 3107-3113.
Kallunski & Tryggvason (Jan. 1992) The Journal of Cell Biology 116(2): 559-571.
Kalsi, et al. (1995) Lupus 4: 375-389.
Lookene, et al. (2000) Biochemistry 39: 230-236.
Lortat-Jacob & Grimaud (1991) FEBS 280: 152-154.
Maher, et al. (1989) Mol. Cell Biol. 9: 2251-2253.
Margalit, et al. (1993) Journal of Biological Chemistry 265(26): 19228-19231.
Mesri, et al. (1994) Journal of Cell Science 107 : 2599-2606.
Ngo, et al. (1995) *The Protein Folding Problem and Tertiary Structure Prediction* pp. 491-495.
Ohta, et al. (Apr. 1994) Free Radical Biology & Medicine 16(4): 501-507.
Olofsson, et al. (1999) Journal of Clinical Investigation.
Pasqualini, et al. (1997) Nature Biotech. 15: 542-546.
Pohl, et al. (1990) FEBS 272: 200-204.
Robinson (1963) Adv. Lip. Res. 1:1 133-182.
Ruoslahti & Yamazuchi (Mar. 1991) Cell 64: 867-869.
Salmivira & Jalkanen (1995) Experentia 51: 863-872.
Stevenson, et al. (1993) J. Autoimmunity 6: 809-825.
Stoll, et al. Journal of Controlled Release 64: 217-218 (2000).
Ternynck, et al. (1987) "Techniques immunoenzymatiques" Editions INSERM.
Weisgraber and Rall (1987) Journal of Biological Chemistry 262(23): 11097-11103.
Xu, et al. (1996) Glycoconjugate Journal 13: 81-90.
Yayon, et al. (Feb. 22, 1991) Cell 64: 841-848.
Requirement for Restriction/Election of Nov. 10, 2005 from U.S. Appl. No. 10/231,889.
Non-Final Rejection of Jun. 27, 2006 from U.S. Appl. No. 10/231,889.
Final Rejection of Apr. 5, 2007 from U.S. Appl. No. 10/231,889.
Non-Final Rejection of Jan. 9, 2008 from U.S. Appl. No. 10/231,889.
Final Rejection of Aug. 5, 2008 from U.S. Appl. No. 10/231,889.

\* cited by examiner

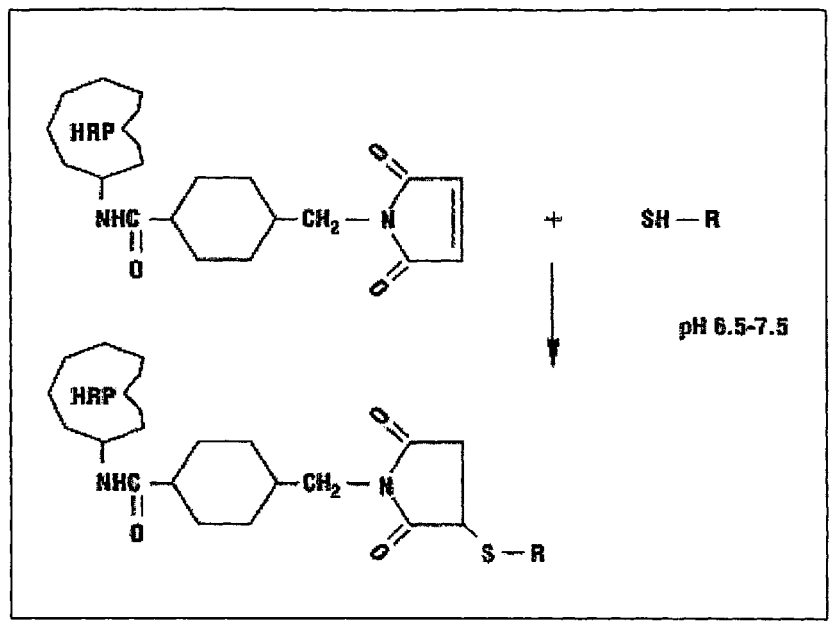
Figure 1
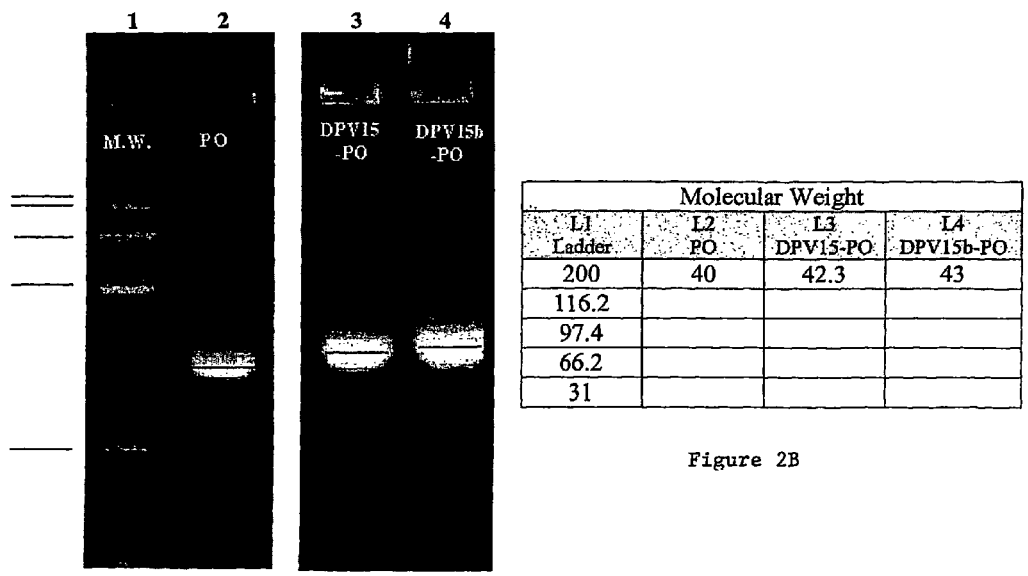
Figure 2A
| Molecular Weight | | | |
|---|---|---|---|
| L1 Ladder | L2 PO | L3 DPV15-PO | L4 DPV15b-PO |
| 200 | 40 | 42.3 | 43 |
| 116.2 | | | |
| 97.4 | | | |
| 66.2 | | | |
| 31 | | | |
Figure 2B Lane 1 : Molecular Weight standard
Lane 2 : AntiPO IgG
Lane 3 : DPV 15-AntiPO IgG conjugate.
Lane 4 : DPV 15b-AntiPO IgG conjugate.

DPV15b-TMR

DPV15b-TMR

SEQUENCE LISTING

```
<160> NUMBER OF SEQ ID NOS: 20

<210> SEQ ID NO 1
<211> LENGTH: 16
<212> TYPE: PRT
<213> ORGANISM: Homo sapiens

<400> SEQUENCE: 1

Leu Arg Arg Glu Arg Gln Ser Arg Leu Arg Arg Glu Arg Gln Ser Arg
1               5                   10                  15

<210> SEQ ID NO 2
<211> LENGTH: 22
<212> TYPE: PRT
<213> ORGANISM: Homo sapiens

<400> SEQUENCE: 2

Gly Ala Tyr Asp Leu Arg Arg Arg Glu Arg Gln Ser Arg Leu Arg Arg
1               5                   10                  15

Arg Glu Arg Gln Ser Arg
            20

<210> SEQ ID NO 3
<211> LENGTH: 14
<212> TYPE: PRT
<213> ORGANISM: Homo sapiens

<400> SEQUENCE: 3

Ser Arg Arg Ala Arg Arg Ser Pro Arg His Leu Gly Ser Gly
```

```
1               5                   10
```

<210> SEQ ID NO 4
<211> LENGTH: 16
<212> TYPE: PRT
<213> ORGANISM: Homo sapiens

<400> SEQUENCE: 4

```
Arg Lys Lys Arg Arg Arg Glu Ser Arg Lys Arg Arg Arg Arg Glu Ser
1               5                   10                  15
```

<210> SEQ ID NO 5
<211> LENGTH: 18
<212> TYPE: PRT
<213> ORGANISM: Homo sapiens

<400> SEQUENCE: 5

```
Arg Lys Lys Arg Arg Arg Glu Ser Arg Arg Ala Arg Arg Ser Pro Arg
1               5                   10                  15

His Leu
```

<210> SEQ ID NO 6
<211> LENGTH: 17
<212> TYPE: PRT
<213> ORGANISM: Homo sapiens

<400> SEQUENCE: 6

```
Gly Arg Pro Arg Glu Ser Gly Lys Lys Arg Lys Arg Lys Arg Leu Lys
1               5                   10                  15

Pro
```

<210> SEQ ID NO 7
<211> LENGTH: 19
<212> TYPE: PRT
<213> ORGANISM: Homo sapiens

<400> SEQUENCE: 7

```
Ser Arg Arg Ala Arg Arg Ser Pro Arg Glu Ser Gly Lys Lys Arg Lys
1               5                   10                  15

Arg Lys Arg
```

<210> SEQ ID NO 8
<211> LENGTH: 15
<212> TYPE: PRT
<213> ORGANISM: Homo sapiens

<400> SEQUENCE: 8

```
Gly Lys Arg Lys Lys Lys Gly Lys Leu Gly Lys Lys Arg Asp Pro
1               5                   10                  15
```

<210> SEQ ID NO 9
<211> LENGTH: 17
<212> TYPE: PRT
<213> ORGANISM: Homo sapiens

<400> SEQUENCE: 9

```
Gly Lys Arg Lys Lys Lys Gly Lys Leu Gly Lys Lys Arg Pro Arg Ser
1               5                   10                  15

Arg
```

<210> SEQ ID NO 10
<211> LENGTH: 19

```
<212> TYPE: PRT
<213> ORGANISM: Homo sapiens

<400> SEQUENCE: 10

Val Lys Arg Gly Leu Lys Leu Arg His Val Arg Pro Arg Val Thr Arg
1               5                   10                  15

Met Asp Val

<210> SEQ ID NO 11
<211> LENGTH: 17
<212> TYPE: PRT
<213> ORGANISM: Homo sapiens

<400> SEQUENCE: 11

Leu Arg Arg Glu Arg Gln Ser Arg Leu Arg Arg Glu Arg Gln Ser Arg
1               5                   10                  15

Cys

<210> SEQ ID NO 12
<211> LENGTH: 17
<212> TYPE: PRT
<213> ORGANISM: Homo sapiens

<400> SEQUENCE: 12

Arg Lys Lys Arg Arg Arg Glu Ser Arg Lys Lys Arg Arg Arg Glu Ser
1               5                   10                  15

Cys

<210> SEQ ID NO 13
<211> LENGTH: 20
<212> TYPE: PRT
<213> ORGANISM: Homo sapiens

<400> SEQUENCE: 13

Cys Val Lys Arg Gly Leu Lys Leu Arg His Val Arg Pro Arg Val Thr
1               5                   10                  15

Arg Met Asp Val
            20

<210> SEQ ID NO 14
<211> LENGTH: 23
<212> TYPE: PRT
<213> ORGANISM: Homo sapiens

<400> SEQUENCE: 14

Cys Gly Ala Tyr Asp Leu Arg Arg Arg Glu Arg Gln Ser Arg Leu Arg
1               5                   10                  15

Arg Arg Glu Arg Gln Ser Arg
            20

<210> SEQ ID NO 15
<211> LENGTH: 18
<212> TYPE: PRT
<213> ORGANISM: Homo sapiens

<400> SEQUENCE: 15

Gly Lys Arg Lys Lys Lys Gly Lys Leu Gly Lys Lys Arg Pro Arg Ser
1               5                   10                  15

Arg Cys

<210> SEQ ID NO 16
```

```
-continued

<211> LENGTH: 19
<212> TYPE: PRT
<213> ORGANISM: Homo sapiens

<400> SEQUENCE: 16

Arg Lys Lys Arg Arg Glu Ser Arg Arg Ala Arg Arg Ser Pro Arg
1               5                   10                  15

His Leu Cys

<210> SEQ ID NO 17
<211> LENGTH: 18
<212> TYPE: PRT
<213> ORGANISM: Homo sapiens

<400> SEQUENCE: 17

Gly Arg Pro Arg Glu Ser Gly Lys Lys Arg Lys Arg Lys Arg Leu Lys
1               5                   10                  15

Pro Cys

<210> SEQ ID NO 18
<211> LENGTH: 16
<212> TYPE: PRT
<213> ORGANISM: Homo sapiens

<400> SEQUENCE: 18

Gly Lys Arg Lys Lys Lys Gly Lys Leu Gly Lys Lys Arg Asp Pro Cys
1               5                   10                  15

<210> SEQ ID NO 19
<211> LENGTH: 15
<212> TYPE: PRT
<213> ORGANISM: Homo sapiens

<400> SEQUENCE: 19

Ser Arg Arg Ala Arg Arg Ser Pro Arg His Leu Gly Ser Gly Cys
1               5                   10                  15

<210> SEQ ID NO 20
<211> LENGTH: 20
<212> TYPE: PRT
<213> ORGANISM: Homo sapiens

<400> SEQUENCE: 20

Ser Arg Arg Ala Arg Arg Ser Pro Arg Glu Ser Gly Lys Lys Arg Lys
1               5                   10                  15

Arg Lys Arg Cys
            20
```

SEQUENCES FACILITATING PENETRATION OF A SUBSTANCE OF INTEREST

CROSS REFERENCE TO RELATED APPLICATIONS

This application is the National Stage Application of International Application No. PCT/IB2004/002936, filed Aug. 13, 2004, which claims the benefit of European Patent Application No. 03292030.8, filed Aug. 14, 2003 and published as EP1512696, the disclosure of which is herein incorporated by reference in its entirety. Applicant herein incorporates French Patent Application No. 0309962, filed Aug. 14, 2003, and published as FR 2858772, by reference in its entirety.

FIELD OF THE INVENTION

The invention relates to the field of method and composition for delivering active substance onto cells and/or cell nuclei. More particularly the invention describes amino acid sequences having the capacity to facilitate penetration of a substance of interest such as a drug into cells and/or cell nuclei.

BACKGROUND

There is a need for composition and method able to transfer substances of interest from the outside medium to the inside of cells, and more specifically cell nuclei. Such composition and method are useful to enhance the delivery of drugs into the cytoplasm and/or the cell nucleus from the host organism being treated. An important application of such composition and method concerns the field of gene therapy where selective and non toxic vectors are necessary for introducing DNA into the cell and more specifically cell nuclei.

Peptides and amino acid sequences have been proposed to transfer substances of interest from the outside medium to the inside of cells. For example, PCT patent application published under No. WO 01/64738, describes amino acid sequences which react with aminoglycans and transfer a broad range of active substances (biological, pharmaceutical, cosmetic, nutritional, diagnostic or tracer) such as nucleic acids, proteins, drugs, antigens or antibodies.

SUMMARY OF THE INVENTION

It has been found now new amino acid sequences which can be used both in vivo and in vitro as agents for internalizing substances of interest into cells. Therefore the present invention relates to an amino acid sequence being able to facilitate penetration of a substance of interest inside cells and/or cell nuclei and having the following formula:

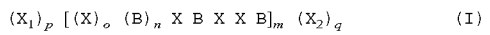

Wherein $X_1$ and $X_2$ are amino acid sequences of 1 to 20 amino acids;

p and q are whole numbers between 0 and 5;

B is a basic amino acid;

X is a non-basic, preferably hydrophobic amino acid, such as alanine, isoleucine, leucine, methionine, phenylalanine, tryptophan, valine or tyrosine;

n is 2 or 3;

m is 1 to 4;

o is 0 or 1.

Generally, the amino acid sequence of formula (I) have less than 100 amino acids, less than 50 amino acids is considered better, and less than 25 amino acids better yet.

Advantageously, the amino acid sequences according to the invention have between 7 and 25 amino acids, preferably between 7 and 15 amino acids and more preferably between 15 and 25 amino acids.

Generally, the amino acid sequence includes a high number of basic amino acids (B) such as lysine, arginine or histidine.

"High number" should be understood as at least equal to 3.

Preferred amino acid sequences according to the invention are those wherein:

o is 1, and/or p or q is 0, and/or

X1 or X2 is a sequence of 2 to 5 amino acids, and/or n is 2 or 3, and or m is 2.

Among them, amino acid sequence especially preferred have the following formula:

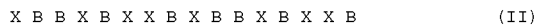

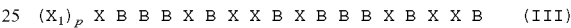

wherein $X_1$, X, B and p have the same meaning as above.

In another embodiment, several or all L-amino acids of the amino acid sequence above may be changed to D-amino acids. In certain preferred embodiment, the N-terminal and/or C-terminal amino acid is a D-amino acid.

Particularly interesting amino acid sequences according to the above formula are:

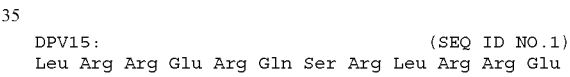

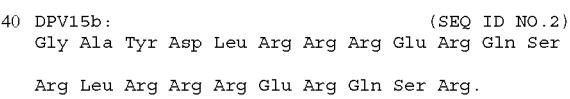

The present invention further relates to the following amino acid sequences which can be used both in vivo and in vitro as agents for internalizing substances of interest into cells:

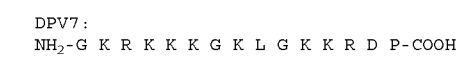

Respectively SEQ ID No 4, 5, 6, 8, 9, 3, 7.

The invention relates to these sequences with or without the C-terminal Cystein. Cystein can be added in C- or N-terminal position of the sequences to conjugate peptides to molecules.

Therefore the present invention relates to the above DPV which can facilitate penetration of a substance of interest inside cells and/or cell nuclei. Definition and detailed description hereafter are directed to both DPV15, DPV15b and DPV3, 3/10, 6, 7, 7b, 10, 10/6.

DEFINITIONS AND DETAILED DESCRIPTION OF THE INVENTION

The above amino acid sequences are capable of reacting in vivo with the aminoglycans or glycoaminoglycans and more particularly with heparin, chondroitine sulfates and their derivatives.

The mechanism for internalization of the peptide (amino acid sequence) according to the invention, and hence of the substances of interest coupled to said peptide, is therefore dependent on energy. The vectorization using the above peptides is therefore remarkable by the fact that it does not come from a passive system. The amino acid sequences according to the invention are therefore characterized by their capacity to react in vivo with the aminoglycans, the glycoaminoglycans, the aminoglycan sulfates, the chondroitines and the chondroitine sulfates, and to cross cell membrane.

The peptides according to the invention are therefore remarkable in that they have the capacity to cross the cell membranes by an active mechanism, then to lodge in the cytoplasm and/or the cell nucleus and thus to make it possible to have a vector whose use is not limited, when it passes into the cell, by the size of the substances being transported. Indeed, the vectors (constituted by or comprising the peptide/amino acid) according to the invention are capable of transporting drugs, ranging from small chemical molecules (low molecular weight) to proteins or plasmid-type nucleic acids (high molecular weight).

The use of these vectors thus opens a new path in intracellular protein therapy or gene therapy. This special capacity of the vectors in the invention for penetration makes it possible to target drugs in the cells in a preferential way, thus contributing to a potential reduction in the toxicity of the drugs and a potential increase in the efficacy index.

"Heparin or chondroitine sulfate derivatives" or "aminoglycans like heparin or chondroitine sulfate" are understood to mean any product or sub-product as defined in the prior art (Cardin A. D. & Weintraub H. J. R. Arteriosclerosis 9:21 (1989); Merton B. et al. Annu. Rev. Cell Biol. 8:365 (1992); David G. FASEB J. 7:1023 (1993)).

"Facilitate penetration" is understood to mean facilitating the passage or translocation of a substance from the outside medium into the intracellular medium, and quite specifically into the cytoplasm and/or the nucleus of the cell. This penetration can be determined by various processes, for example by a cell penetration test having a first incubation step for the amino acid sequence in the presence of culture cells, followed by a fixing step and permeabilization of those cells, and then revelation of the presence of said amino acid sequence inside the cell. The revelation step can be done with another incubation in the presence of antibodies marked and directed against said sequence, followed by detection in the cytoplasm or in immediate proximity of the cell nucleus, or even within it, of the immunologic reaction between the sequence and the marked antibodies. Revelation can also be done by marking an amino acid sequence in the invention and detecting the presence of said marking in the cell compartments. A cell penetration test was described in patent application No. WO 97/02840.

"Substance of interest" is understood to mean any product presenting an interest, particularly biological, pharmaceutical, diagnostic, tracing, or agro-food. They can be nucleic acids (DNA, RNA, siRNA, dsRNA, ssRNA, aRNA) that can have various origins, and particularly, human, viral, animal, eukaryotic or prokaryotic, vegetable, synthetic, etc., and able to vary in size, ranging from a simple oligonucleotide to a genome or genome fragment. It can also be a viral genome or plasmid. The substance can also be a protein, such as an enzyme, a hormone, a cytokine, an apolipoprotein, a growth factor, an antigen, an antibody, etc. It can also be a toxin, antibiotic, antiviral molecule or immune modulator. It can also be a polymer-type component, such as a microsphere or a nanosphere.

Generally, the substance of interest can be any active ingredient of a drug, whether it is a chemical, biochemical, natural or synthetic product. The molecules can be small, with a molecular weight of around 500 D, or large like proteins of several thousand Daltons. But the active ingredient can be also a marker such as a fluorochrome for example Tetra-Methyl-Rhodamine (TMR).

The substance of interest can be directly active or can be activated in situ by a distinct agent or by environmental conditions. The scope of the invention extends to combinations of the amino acid sequence with a substance of interest as defined above.

Another preferred type of sequences according to the invention is constituted by i) a first amino acid sequence as defined above and ii) a second amino acid sequence corresponding to an antibody fragment.

In that embodiment, the first amino acid sequence is coupled (directly or indirectly linked) to the second amino acid sequence.

The second amino acid sequence (peptide) derives advantageously from the variable part of human anti-DNA antibodies.

The coupling of the amino acid sequences and peptides derived from variable parts of human anti-DNA antibodies inside one and the same molecule results in the preparation of a peptide vector that is particularly effective in translocation and intracellular transfer of substances of interest.

This combination also gives rise to a translocation and transfer vector specially adapted for use in humans. Indeed, as indicated above, although the peptide vectors of murine origin known from WO 97/02840 are coded by the germinal line and carry no mutations, and consequently should be close to those encountered in humans in terms of antigens, it is possible that their injection into humans would induce an immune reaction. The peptide vector formed from amino acid sequences according to the invention and from peptides derived from anti-DNA antibodies prevents this problem.

The general characteristics of these peptides derived from human anti-DNA antibodies are close to those of the peptides of murine origin described in patent application WO 99/07414, while they have additional properties that distinguish them from the latter, namely:

1) To penetrate inside cells, they have to have an active cell metabolism (culture temperature between 25° C. and 39° C., preferably and 37° C.), while the murine peptides are clearly less dependent;

2) They react much less strongly with DNA than the murine vectors;

3) Their penetration capacity is not significantly influenced by the molecule they are going to transport inside the cell;

4) They penetrate better inside cells of human origin than inside cells of other origins.

The amino acid sequences (peptides) as defined above are capable of transporting inside cells molecules that are combined with them covalently or non-covalently, and are thus effective vectors for intracellular transfer of the substances of interest.

As shown in the example relating to internealization of DPV-antiPO IgG (see FIGS. 18 and 42), the peptides according to the invention are capable of transporting inside cells molecules that remain active once inside the cells.

Therefore, the present invention is aimed at using the amino acid sequences defined above to prepare compositions designed to transfer substances of interest into cells. This capacity of the peptides in the invention is an advantage to allow the transport of active substances through biological membranes and, quite specifically, through the hematoencephalic, hematoretinal, intestinal and pulmonary barriers. The peptides in the invention have the interest of being able to be used in forms of administration adjusted to both the active substance to which they are coupled and to the type of cell targeted, particularly those requiring passage through the above barriers.

In another embodiment, the present invention relates to the use of said amino acid sequences as a peptide vector. These vectors, due to the properties of said amino acid sequences, can be used easily for intracytoplasmic, intracytosolic and/or intranuclear transfer in humans, with no risk to them or any degradation of the substance of interest coupled to the vector.

A vector according to the present invention is characterized by the fact that it is composed of, or includes, an amino acid sequence as defined above.

As indicated above, a vector may also comprise one or more antibody fragments, preferably polyreactive, and more specifically one or more fragments that come from hypervariable regions of the antibody, linked to an amino acid sequence according to the invention. Preferably, the vector that is the subject of the invention is characterized by the fact that it contains a fragment of the heavy chain of an antibody.

The subject of the present invention is a vector for cell internalization, characterized by the fact that it contains one or more amino acid sequences according to the invention and one or more fragments of an IgM or an IgG.

Preferably, said vector contains all or part of the CDR2 region of an antibody. As a variation, said vector contains all or part of the CDR3 region of an antibody. More specifically, said vector contains at least one CDR3 region of an anti-DNA human antibody, selected from the group consisting of RTT79, NE-1 and RT72.

In another embodiment, the vector can also contain all or part of region CDR2, and all or part of region CDR3.

By "all or part" it is understood that the vector can contain either the whole CDR region concerned, or only part of it, provided that the vector retains the capacity to penetrate into the cells (functional homologue). By "part of CDR region" is understood a CDR region deprived of one or more terminal amino acids. It can also be a CDR region in which one or more internal residues have been deleted or substituted for other amino acids, preferably amino acids of the same nature (basic amino acids, for example).

As indicated above, the vector in the invention is particularly well suited for intracellular and intranuclear transport and transfer of substances of interest.

The present invention is therefore aimed at supplying a vector such as the one described above, characterized by the fact that it contains a substance that can be incorporated into the cells and/or the nuclei of said cells.

More specifically, the present invention is directed to a vector whose penetration capacity is quite independent from the nature of the substance of interest that is coupled to it. This characteristic, proper to these human vectors compared to the murine vectors, is of primary interest in the planned use of these vectors. But the invention is also interested in vectors that are adapted to the substance of interest which is coupled to it.

"Coupling" is understood to mean any type of interaction allowing a physical association between the substance of interest and the vector. It can be cleavable or non-cleavable according to the biological medium and/or the substance of interest transported by the peptides of the invention or it can be cleavable by physical means applied to the organism to which the vector coupled to the active substance has been administered. Thus, the expression of the biological effect of the substance can require that it be released from the vector. Doxorubicin can be cited as an example of a substance of interest that is preferably released from the vector.

However, the interaction must be solid enough that the vector does not dissociate before or during cell penetration. For this reason, the coupling preferred in the invention is covalent coupling, although it can be non-covalent coupling. The substance of interest can be coupled directly to the peptide either on one of those terminal ends (N- or C-terminal end) or on a side chain or one of the amino acids. The substance of interest can also be coupled indirectly by a connecting arm either to one of the terminal ends of the peptides or to a side chain of one of the amino acids. To facilitate the covalent coupling a cystein residue may be added to the amino acid sequence either on one of those terminal ends or to any position of the said amino acid sequence.

The coupling can be done by any chemical, biochemical, enzymatic or genetic coupling process known to a person skilled in the art, but it is generally preferred to use a homofunctional or heterofunctional bridging reagent like succinimidyl 4-(N-maleimidomethyl) cyclohexane-1-carboxylate (SMCC). Other coupling means that can be cited are those chosen from among: bi-functional or multi-functional agents containing alkyl, aryl, aralkyl or peptide groups; esters; aldehydes or alkyl, aryl or aralkyl acids; anhydride, sulfhydrile or carboxyl groups such as maleymil benzoic acid and maleymil propionic acid derivatives and succinimidyl derivatives; groups derived from bromide or cianogenic chloride, carbonyldiimidazole, succinimide esters or sulphonic halogenides.

In another form of embodiment of this invention, said substance of interest can also be coupled by any genetic engineering technique known to a person skilled in the art. "Genetic engineering" means using an expression vector in which the DNA coding for peptide vectors is cloned in phase in 5' and/or 3' of the complementary DNA of the gene of interest. Expression of the fusion protein is under the control of a promotor. The expression system can be used in a prokaryotic or eukaryotic host cell for the production of the fusion protein.

In a first embodiment, said substance of interest is coupled at the N-terminal end of the amino acid sequence of the amino acid sequence according to the invention. In a second embodiment, said substance of interest is coupled at the C-terminal end of said sequence.

Surprisingly, it has been shown that the vector according to the present invention is capable of potentiating the biological activity and, potentially, reducing the toxicity of said coupled substance. More particularly, the use of the vector offers the possibility to overcome the drug resistance developed by a subject against an active substance such as an anti-cancer molecule.

This invention therefore also has as its subject a vector characterized by the fact that it makes it possible to increase the biological activity of the substance of interest to which it is coupled.

It has also been shown that the vector that is the subject of the invention permits transfection of cells in vitro.

In one particular embodiment of the invention, the vector is coupled to the substance of interest by at least one molecule, called an "anchoring molecule", that has a strong natural affinity for the substance of interest to be internalized. The natural affinity of the anchoring molecule for the substance of interest allows the transporter to interact non-covalently with said substance of interest, and hence to carry it along in intracellular travel.

Another especially interesting advantage of this type of transporter consists of the fact that, due to the natural affinity of the anchoring molecule for the substance of interest, these two elements are coupled in a totally natural way, with no chemical or biochemical interaction.

This type of transporter is particularly interesting in a case where the substance of interest, due to its size and/or its structure, proves difficult to couple directly to the amino acid sequence. This type of transporter can also prove particularly useful when the substance of interest is not very stable, and when any kind of chemical interaction for coupling it could degrade it or alter its activity.

In addition, the transporter cannot be specific for a single substance of interest, but can, on the contrary, permit internalization of several different substances of interest inside cells and/or cell nuclei.

The present invention also concerns eukaryotic cells that contain an amino acid sequence as defined above. It also concerns eukaryotic cells that contain an amino acid sequence, a vector and/or a transporter according to the invention. It also concerns any type of eukaryotic cell that has been transfected by a vector and/or transporter according to this invention.

The invention also relates a process to transfer a substance of interest inside a cell in vitro and to increase the biological activity of said substances of interest that has the following steps:

a) coupling the substance to an amino acid sequence, to a vector or to a transporter according to the invention, as described above, and b) incubating the cell with said coupling product at a culture temperature that permits active metabolism of said cell.

Such a temperature is between 25° C. and 39° C., preferably 37° C.

This invention is also directed to a composition having as active ingredient either amino acid sequences, vectors or transporters "loaded" with at least one substance of interest, or eukaryotic cells that have been transfected according to the invention. Its subject is also the use of such compositions for the formulation and preparation of biological, pharmaceutical, cosmetic and agro-food products.

The term "loaded" refers, as indicated above, to an amino acid sequence, vector or transporter according to the invention, linked directly or undirectly, or conjugated with at least one substance of interest.

The scope of the invention extends to pharmaceutically acceptable alkaline or acidic addition salts, hydrates, esters, solvates, precursors, metabolites or stereoisomers, of said vectors and transporters loaded with at least one substance of interest. The scope of the invention also extends to pharmaceutical formulations having a vector or transporter loaded with at least one substance of interest in combination with a pharmaceutically acceptable vehicle, diluent or excipient.

The expression "pharmaceutically acceptable salts" refers to non-toxic salts of the amino acid sequences in the invention that can generally be prepared by having the free base react with a suitable organic or inorganic acid. These salts retain their biological efficacy and the properties of the free bases. Representative examples of said salts that can be cited are water-soluble and water-insoluble salts, such as acetates, ansonates (4,4-diaminostilbenes-2,2'-disulfonates), benzene sulfonates, benzonates, bicarbonates, bisulfates, bitartrates, borates, bromides, butyrates, calcium edetates, camsylates, carbonates, chlorides, citrates, clavulariates, dichlorohydrates, edetates, edisylates, estolates, esylates, fumarates, gluceptates, gluconates, glutamates, glycolylarsanylates, hexafluorophosphates, hexylresorcinates, hydrabamines, hydrobromides, hydrochlorides, hydroxynaphthoates, iodides, isothionates, lactates, lactobionates, laurates, malates, maleates, mandelates, mesylates, methyl bromides, methyl nitrates, methyl sulfates, mucates, napsylates, nitrates, 3-hydroxy-2-naphthoates, oleates, oxalates, palmitates, pamoates (1,1-methylene-bis-2-hydroxy-3-naphtoates, emboates), pantothenates, phosphates/diphosphates, picrates, polygalacturonates, propionates, p-toluene sulfonates, salicylates, stearates, subacetates, succinates, sulfates, sulfosalicylates, suramates, tannates, tartrates, teoclates, tosylates, triethiodides, valerates and salts of N-methylglucamine ammonium.

A subject can be treated with a pharmaceutically effective quantity of a peptide, a vector or a transporter according to the invention, loaded with at least one substance of interest. The expression "pharmaceutically effective quantity" means a quantity capable of making the substance of interest penetrate sufficiently to induce the biological or medical response of a tissue, system, animal or human as expected by the researcher or attending physician.

The invention also covers pharmaceutical compositions suitable for the introduction of a substance of interest into a cell or cell nucleus. The compositions contain an effective quantity of aan amino acid sequence, a vector or a transporter according to the invention, "loaded" with at least one substance of interest, alone or in combination with one or more pharmaceutically acceptable supports. The compositions are particularly useful in the sense that they have very low toxicity, or are non-toxic.

The vectors or transporters according to the invention, or their salts, "loaded" with at least one substance of interest, can be administered by any of the routes of administration accepted for therapeutic agents. These processes include systemic administration, for example oral, nasal, parenteral or topical administration, for example transdermal or even central administration, for example by the intracranial surgical route or intraocular administration.

Oral administration can be used by means of tablets, gel capsules, soft capsules (including delayed or extended-release formulations), pills, powders, granules, elixirs, tinctures, suspensions, syrups and emulsions. This form of presentation is particularly suitable for passage through the intestinal barrier.

Parenteral administration is generally done by subcutaneous, intramuscular or intravenous injection or by perfusion. The injectable compositions can be prepared in the traditional forms, either in suspension or liquid solution or in solid form for extemporaneous dissolution in a liquid. This form of presentation is more specifically adapted for passage through the hematoencephalic barrier.

One possibility of parenteral administration uses implantation of a slow or extended-release system that makes sure a constant dosage level is maintained, for example according to U.S. Pat. No. 3,710,795.

For intranasal administration, suitable intranasal vehicles can be used.

For transdermal administration, transdermal cutaneous stamps well known to a person skilled in the art can be used. A transdermal-release system permits continuous administration.

Other preferred topical preparations include creams, unguents, lotions, aerosol sprays and gels.

Based on the planned route of administration, the compounds can come in solid, semi-solid or liquid form.

For the solid compositions, such as tablets, pills, powders or granules in the free state or included in gel caps, the active ingredient can be combined with: a) diluents, for example lactose, dextrose, sucrose, mannitol, sorbitol, cellulose and/or glycine; b) lubricants, for example silicone, talc, stearic acid, its magnesium or calcium salt and/or polyethylene glycol; c) binders, for example magnesium and aluminum silicate, starch paste, gelatin, tragacanth gum, methyl cellulose, sodium carboxymethyl cellulose and/or polyvinyl pyrrolidone; if necessary, d) disintegrators, for example, starch, agar, alginic acid or its sodium salt, or effervescent mixtures; and/or e) absorbents, dyes, aromatic agents and sweeteners. The excipients can be, for example, mannitol, lactose, starch, magnesium stearate, sodium saccharine, talc, cellulose, glucose, sucrose, magnesium carbonate and pharmaceutical quality analogs.

For semi-solid compositions, such as suppositories, the excipient can be, for example, an emulsion or fatty suspension, or one with a polyalkylene glycol base, such as polypropylene glycol.

The liquid compositions, particularly injectables or those to be included in a soft capsule, can be prepared, for example, by dissolution, dispersion, etc. of the active ingredient in a pharmaceutically pure solvent such as, for example, water, physiological serum, aqueous dextrose, glycerol, ethanol, an oil and the like.

The amino acid sequence, vectors or transporters according to the invention, "loaded" with at least one substance of interest, can also be administered in the form of liposome-type release systems, such as in the form of small unilamellar vesicles, large unilamellar vesicles and multilamellar vesicles. The liposomes can be made from a variety of phospholipids, containing cholesterol, stearoylamine or phosphatidyl cholines. In one form of embodiment, a film of liquid components can be hydrated with an aqueous solution of the drug to form a lipid layer encapsulating the medication, as described in U.S. Pat. No. 5,262,564.

It can be sterilized and/or contain adjuvants and non-toxic auxiliary substances, such as preserving, stabilizing, wetting or emulsifying agents, agents promoting dissolution, salts to regulate osmotic pressure and/or buffers. They can also contain other substances that have therapeutic interest. The compositions are prepared, respectively, by traditional mixing, granulating or coating processes, and they contain around 0.1% to 75%, preferably around 1% to 50% active ingredient.

The amino acid sequences, vectors or transporters of the invention, "loaded" with at least one substance of interest, can also be coupled with soluble polymers, such as targetable drug supports. Such polymers can contain polyvinyl pyrrolidone, pyrane copolymer, polyhydroxypropyl-methacrylamide-phenol, polyhydroxy-ethyl-aspanamide-phenol or poly (ethylene oxide)-polylysine substituted with palmitol residues. The compounds in this invention can also be coupled to a class of biodegradable polymers useful in producing controlled release of a drug, for example, poly(lactic acid), poly (epsilon-caprolactone), poly(hyroxybutyric acid), the poly-ortho esters, the polyacetals, the polydihydropyranes, the polycyanoacrylates and the reticulated or amphipathic sequenced hydrogel copolymers.

The dosage for the administration of the amino acid sequences vectors or transporters of the invention, loaded with at least one substance of interest, is chosen depending on a diversity of factors including the type, species, age, weight, sex and medical condition of the subject; the seriousness of the condition being treated; the route of administration; the status of the subject's kidney and liver functions, and the nature of the particular compound or salt used. A regularly experienced physician or veterinarian will easily determine and prescribe the effective quantity of the vector or transporter loaded with the substance of interest in order to prevent, thwart or stop the progress of the medical condition being treated.

Any of the above pharmaceutical compositions can contain from 0.1% to 99%, preferably 1% to 70%, of the active ingredient.

As examples, the oral dosages of the amino acid sequences, vectors or transporters of the invention, loaded with at least one substance of interest, when they are used for the effects indicated, will be between around 0.05 and 1,000 mg/day by the oral route and, preferably come in the form of tablets containing 0.5, 1.0, 2.5, 5.0, 10.0, 15.0, 25.0, 50.0, 100.0, 250.0, 500.0 and 1,000.0 mg of active ingredient. The effective plasma levels of the vectors or transporters loaded with at least one substance of interest will range from 0.002 mg to 50 mg per kilogram of body weight and per day.

The amino acid sequences, vectors or transporters of the invention, loaded with at least one substance of interest, may be administered in the form of single daily doses, or the total daily dose may be administered in two, three or four doses per day.

In one particular application, the present invention relates to a diagnostic agent for in vitro use, composed of or containing at least one amino acid sequence, vector, transporter and/or one cell according to the invention. Such a diagnostic agent can also be used in vivo.

The subject of this invention is therefore also a diagnostic kit that includes said diagnostic agent. More specifically, the diagnostic kit includes a predetermined quantity of a composition according to the invention, in one or more containers.

Similarly, the amino acid sequence in the invention, or a vector and/or a transporter containing that amino acid sequence, or cells transfected with the help of said vector, can be used in vivo for preventative purposes, for example and in a non-limiting way, for the prevention of viral infections, metastases, cell apoptosis (degenerative diseases, tissue ischemia . . . ), or for therapeutic purposes, for example the treatment of infectious diseases (viral, bacterial . . . ), cancer and pathological neo-angiogenesis.

BRIEF DESCRIPTION OF THE FIGURES

FIG. 1 shows EZ-Link Maleimide Activated Horseradish Peroxidase. M.W=40.000. R represents either DPVs or cysteine.

FIG. 2 shows example of SDS-PAGE separation of the DPV-PO conjugates. A: 15 µg of each DPV-HRP conjugate was loaded on a 10% SDS-PAGE gel. B: molecular weight calculation for each conjugate (Bioprofil software).

EXAMPLES

Figure 3:
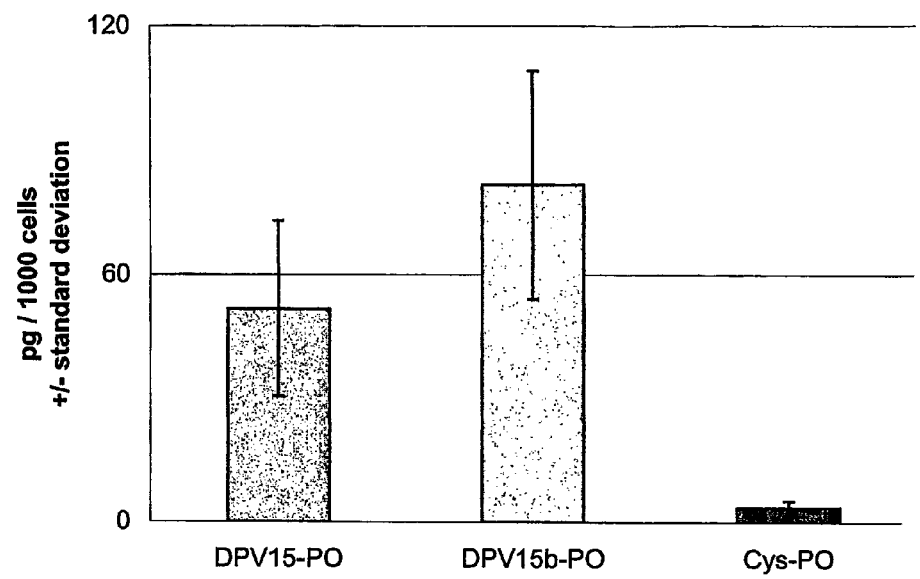
FIG. 3 shows quantitative penetration of the DPV-PO conjugates in HCT116 cells.

Other advantages and characteristics of the invention will appear from the following examples which refer to the above figures. The examples are given to illustrate the invention but not to limit the scope of the claims.

Example 1

Internealization of Control Molecule without Biological Effect (Peroxidase)

1) Materials and Methods.

1.1) Nature of the Ligand.

Peroxidase was chosen to represent the capacity of the DPV15 and DPV15b to internalize medium size proteins (40 000 Da). The use of a preactivated form of the protein allows the preparation of homogenous conjugates (only 1 DPV per PO molecule). Penetration of DPV-PO conjugates was tested in both HCT116 (colorectal carcinoma) and HeLa (cervix adenocarcinoma) cell lines.

EZ-Link Maleimide Activated Horseradish Peroxidase (Pierce 31485) (FIG. 1).

EZ-Link Maleimide Horseradish Peroxidase (PO) (M.W=40.000) is used for an easy preparation of peroxidase conjugates. It is a pre-activated and stable PO derivative that reacts with sulfhydryl (—SH) groups. This product can be used to conjugate PO to any ligand that contains a free —SH group.

Peptide Vectors.

DPV15: Leu Arg Arg Glu Arg Gln Ser Arg Leu Arg Arg Glu Arg Gln Ser Arg (SEQ ID NO.1) with a cystein residue at its C terminal end for coupling a substance of interest, DPV15b: Gly Ala Tyr Asp Leu Arg Arg Arg Glu Arg Gln Ser Arg Leu Arg Arg Arg Glu Arg Gln Ser Arg (SEQ ID NO.2) with a cystein residue at its N terminal end for coupling a substance of interest, DPV15 and DPV15b may comprise a cystein residue at one or both of their N or C terminal ends for coupling a substance of interest, DPV10: Ser Arg Arg Ala Arg Arg Ser Pro Arg His Leu Gly Ser Gly (SEQ ID NO.3) with a cystein residue at its C terminal end for coupling a substance of interest (this sequence has been disclosed in the PCT patent application published under No. WO 01/64738).

Vivaspin (Vivascience):

Ultrafiltration membrane (6 mL/cutoff threshold=10000 Daltons), used for concentration and purification of the conjugated compounds (elimination of excess reagent).

Free Peroxidase (SIGMA ref P-6782) used for controls.

1.2) Conjugation Protocol.

Dissolve 500 µg of DIATOS peptide in 50 µl of conjugation buffer (NaCl 0.5M, Sodium phosphate 50 mM, EDTA 5 mM pH 7).

Dissolve 1 mg of Maleimide Activated Peroxidase in 200 µl of conjugation buffer.

Add 43 µl of DIATOS peptide to 1 mg (200 µl) of Maleimide Activated Peroxidase (Molar Ratio: 5 pept/PO-Maleimide)

Mix and incubate 3 hours at room temperature

Add 1 ml of 0.5M NaCl

Concentrate DPV-PO with vivaspin. Centrifugation 10-15 min, 3300 g, 20° C.

Refill vivaspin with 2 ml of 0.15 M NaCl and concentrate conjugate again

Repeat this last step one time.

A control was made which consists of PO linked to Cystein.

1.3) Conservation of the Conjugates.

DPV-PO conjugates are kept frozen (−20° C.), diluted in 0.15 M NaCl.

1.4) Characterization of the Conjugated Compounds.

a) SDS-PAGE.

15 µg of each sample are loaded on a 10% acrylamide SDS-PAGE gel.

Migration 100 V—1 hour.

Staining of the gel with brilliant blue coomassie solution for 1 hour.

Destaining for 1 hour in $H_2O$/Ethanol/Acetic acid. (6V/3V/1V).

FIG. 2A shows an increase of molecular weight after coupling (band 1 is lower in lane 2 than in lanes 3 and 4). The table in FIG. 2B shows the result of calculation of the conjugates molecular weight with the bioprofil software. For every conjugate, there is an increase of approximately 2 kDa, corresponding to the molecular weight of the DPVs that were added to the PO molecule. The presence of a single band in lanes 3 and 4 shows that the only molecule in solution is actually DPV-PO conjugate, and that there is no free PO in solution.

b) ELISA Test on Heparin Coated Plates.

DPV-PO conjugates and controls (free PO and Cys-PO) are loaded on an ELISA plate previously coated with 5 µg/ml heparin (so that only conjugated compounds will bind and react with PO substrate).

Diluted samples (30 ng/ml) are incubated 1 hour at 37° C., and washed 5 times in PBS containing 0.1% Tween.

Staining is obtained with PO substrate (O-Phenylenediamine Dihydrochloride (OPD) (Sigma) tablets)—5 mg pills diluted in 10 ml citrate-citric acid buffer 0.1 M+100 µl $H_2O_2$ 3%).

Reaction is stopped by addition of 50 µl $H_2SO_4$ 2N.

O.D. read at 490 nm.

This test allows the detection of conjugate in solution, as another verification of the results shown in FIG. 2A. However, it does not allow its quantification, possible only after the experiment described in II.4.c.

c) Determination of the Concentration of the Conjugated Compounds in Solution.

The quantification of DPV-PO conjugates in solution is realized after verification of a proper coupling by Elisa, and is based on the activity of the PO protein itself, assuming that there is no free peroxidase in solution.

Standard dilutions for free PO (from 10 ng/ml, then_dilutions).

Dilution of the DPV-PO samples 1/160 000, then_dilutions.

50 µl of solution in a well of a 96 well Elisa plate.

Add PO substrate (OPD).

Stop reaction after 9 min by addition of 50 µl $H_2SO_4$ 2N.

Read O.D. at 490 nm and compare with the one obtained for free PO.

1.5) Internalization Protocol.

Internalization experiments were realised in both HCT116 (colorectal carcinoma) and Hela (cervical adenocarcinoma) cell lines. Internalization was initially evaluated at a single time point (4 hours).

HCT116 culture medium: Mc Coy's 5a (Gibco BRL)+1.5 mM L-glutamine+10% SVF.

HeLa culture medium: DMEM (Gibco BRL)+2 mM L-glutamine+1 mM Na Pyruvate+10% SVF.

a) Quantitative Assay.

Cells were routinely seeded at Day 0: $3.6.10^4$ cells/cm² for HeLa cells, or $7.10^4$ cells/cm_ for HCT116 cells, in 8 wells labtek glass slides (0.7 cm²/well). Penetration studies are performed at Day1.

Protocol:

Dilute conjugates in DMEM+10% FCS at 75 µg/ml.

Take culture medium off the cells Incubate conjugates for 4 hours, 37° C., 5% $CO_2$—100 µl/well (i.e. 7.5 µg/well).

Rinse cells 3 times in PBS.

Incubate the cells in 100 µl Trypsin-EDTA for 30 min at 37° C.

Resuspend cells in 150 µl of complete culture medium.

Count cells.

Centrifuge and rinse cells twice in ice cold PBS.

Resuspend in 220 µl cold lysate buffer (0.1M Tris pH8, 0.5% NP40).

Incubate 15 min at 4° C.

Centrifuge cell lysates.

Distribute 100 µl per well in a 96 wells plate.

Prepare a peroxidase standard curve in lysis buffer (from 10 ng/ml. Diluted in PBS. 10 points). Count the tested solution, to calculate % of internalization.

Add soluble peroxidase substrate (1 pill of 5 mg OPD (Sigma)+10 ml citrate-citric acid buffer 0.1 M, pH5.5+100 µl 3% $H_2O_2$)

Stop the reaction after 9 min by adding 50 µl $H_2SO_4$ 2 N.

Read absorbance at 490 nm.

b) Qualitative Evaluation of the Internalization of DPV-PO Conjugates.

Cells were routinely seeded at Day 0 on 8 wells glass labteck slides (1 cm²) in the following conditions: $0.3 \cdot 10^5$ cells/well for CHO cells (murine ovarian cells), $0.25 \cdot 10^5$ cells/well for PgsA-745 cells (murine ovarian cells deficient in glycosaminoglycans (GAG) expression and HeLa cells. Seeding was always performed in 250 µl of medium. Penetration studies are routinely performed at Day 1 for all these cell lines.

Protocol:

Dilute conjugates in DMEM+10% SVF at the proper concentration.

Take culture medium off the cells

Incubate conjugates in the proper conditions.

Rinse cells 3 times in PBS.

Fix in 3.7% PFA for 20 min at room temperature (RT).

Rinse in PBS at RT.

Perform the immunostaining with the proper antibodies, the secondary being conjugated to a fluorochrome.

Mount in the presence of Dapi.

2) Results.

2.1) Quantitative Intracellular Accumulation.

FIG. 3 shows quantitative penetration of the DPV-PO conjugates in HCT116 cells. Cell lysis was performed after 4 hours of incubation at an initial DPV-PO conjugates concentration of 75 μg/ml (corresponding to approximately 1.8 μM). Results are given as the mean value obtained in three independent experiments, all realized in duplicates.

Table 1 represents net quantities of DPV-PO conjugates internalized in HCT116 cells. Results are given in picograms PO/1000 cells.

TABLE 1

|  | pg PO/1000 cells | standard deviation |
| --- | --- | --- |
| DPV15-PO | 52 | 21 |
| DPV15b-PO | 82 | 28 |
| Cys-PO | 4 | 2 |

Figure 4:
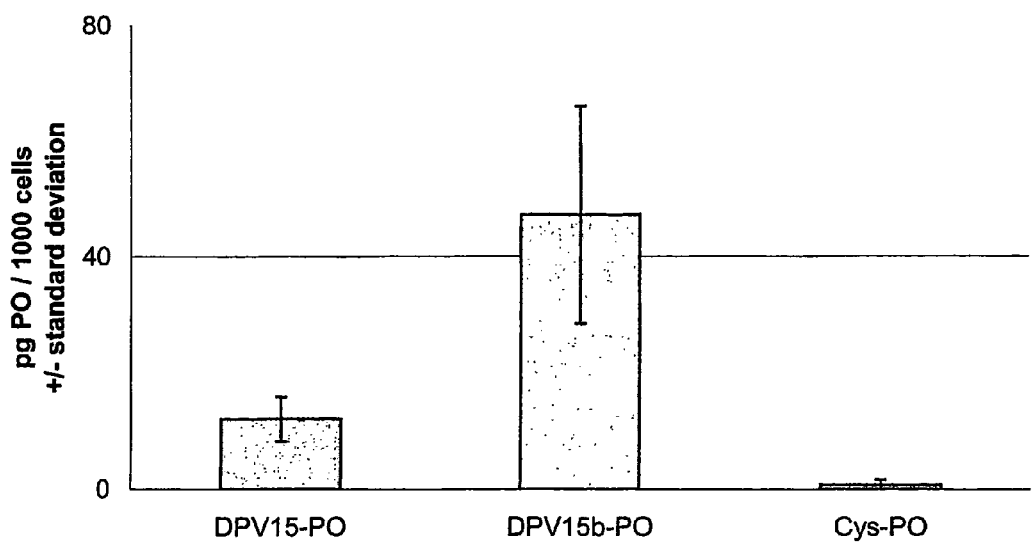
FIG. 4 shows quantitative penetration of the DPV-PO conjugates in HeLa cells.

FIG. 4 shows quantitative penetration of the DPV-PO conjugates in HeLa cells. Cells were incubated for 4 hours in the presence of the conjugates at an initial concentration of 75 μg/ml. Results are given as the mean value obtained in three independent experiments, all realized in duplicates.

Table 2 represents net quantities of DPV-PO conjugates internalized in HeLa cells. Results are given in picograms/1000 cells.

TABLE 2

|  | pg PO/1000 cells | standard deviation |
| --- | --- | --- |
| DPV15-PO | 12 | 4 |
| DPV15b-PO | 47 | 19 |
| Cys-PO | 1 | 1 |

Figure 5:
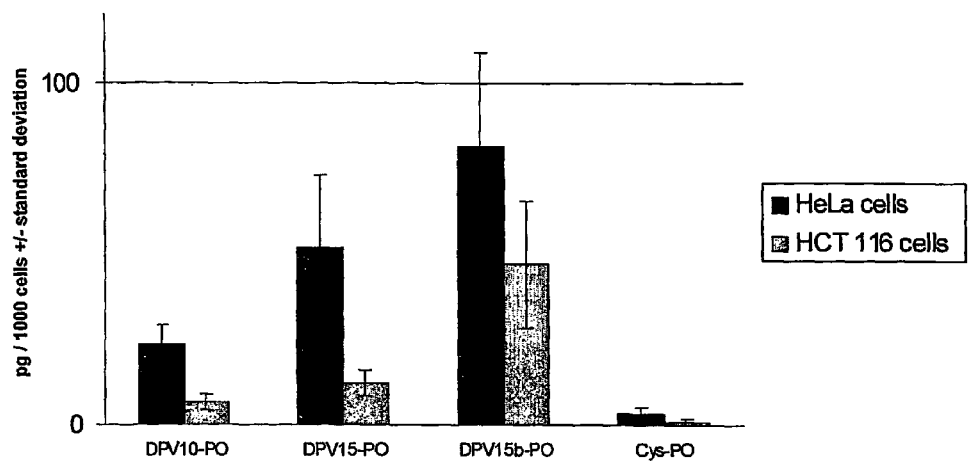
FIG. 5 shows the comparison of the level of internalization of the DPV15-PO, DPV15b-PO and DPV10-PO conjugates in HeLa and HCT116 cells.

FIG. 5 shows the comparison of the level of internalization of the DPV-PO conjugates in HeLa and HCT116 cells.

Table 3: Estimated number of conjugate molecules internalized in each cell type (million conjugate molecules per cell) and ratio of intracellular accumulation of DPV-PO conjugates in HeLa versus HCT116 cells.

TABLE 3

|  | HeLa millions mol/cellule | HCT116 millions mol/cellule |
| --- | --- | --- |
| DPV15-PO | 0.7 | 0.2 |
| DPV15b-PO | 1.2 | 0.7 |

As can be seen in FIGS. 3-5 and table 1-3, the level of DPV-PO intracellular accumulation is variable, as a function of the DPV, and as a function of the cell line.

2.2) Qualitative Evaluation of the Internalization of DPVs-Peroxidase in HeLa Cells.

DPV-PO conjugates were incubated with HeLa cells cultivated on glass labtek slides (4 hours incubation of a 75 μg/ml solution in DMEM+10% FCS, at 37° C.). The experiment was realized with the same peptide-PO conjugates as the ones used in the quantitative experiments described above, in the exact same conditions.

Figure 6:
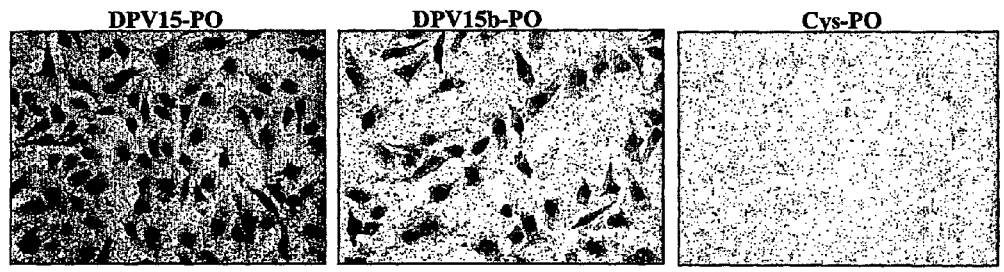
FIG. 6 shows localization of the DPV-PO conjugates in HeLa cells.

FIG. 6 shows localization of the DPV-PO conjugates in HeLa cells.

DPV-PO conjugates were incubated for 4 hours at an initial concentration of 75 μg/ml on HeLa cells, on 8 wells labtek glass slides. Revelation of peroxidase was performed using di-aminobenzidine, as described in section III-2. Pictures were taken with a Nikon coolpix numeric camera, maximum zoom, after visualization on a Leica microscope (20×lens+0.63× adaptator).

FIG. 6 shows typical images of what can be observed after penetration of the conjugates in HeLa cells and di-aminobenzidine (DAB) revelation of peroxidase. DPV15-PO and DPV15b-PO were clearly always mainly nuclear.

Figure 7:
FIG. 7 shows immunofluorescent staining of DPV15b-PO and DPV15-PO conjugates after internalization in HeLa cells for 4 hours at 37° C.

FIG. 7 shows details of HeLa cells after DPV15b-PO internalization. Pictures were taken in the same conditions as described above for FIG. 6. Numeric enlargement was obtained afterwards.

FIG. 7 shows more precisely what can be observed. For DPV15b-PO, nuclei and nucleoli are clearly stained and the cytoplasm is also stained, though much more weakly.

FIG. 7 shows immunofluorescent staining of DPV15b-PO and DPV15-PO conjugates after internalization in HeLa cells for 4 hours at 37° C. DPV-PO conjugates were incubated for 4 hours at an initial concentration of 75 μg/ml on HeLa cells, on 8 wells labtek glass slides. Revelation of peroxidase was performed using a primary monoclonal antibody against peroxidase, and a secondary anti mouse TRITC-conjugated antibody.

2.3) Influence of the Initial Concentration on the Level of Intracellular Accumulation.

All the preliminary experiments concerning the internalization of DPV-PO conjugates had been realized at an initial conjugate concentration of 75 μg/ml. In order to verify if the internalisation mechanism could be saturated, the influence of the initial conjugate concentration on the level of intracellular accumulation of the conjugates was studied.

The internalization (FIG. 8) of DPV15b-PO and DPV15-PO shows that no plateau is reached within the range of concentrations that were tested.

Figure 8:
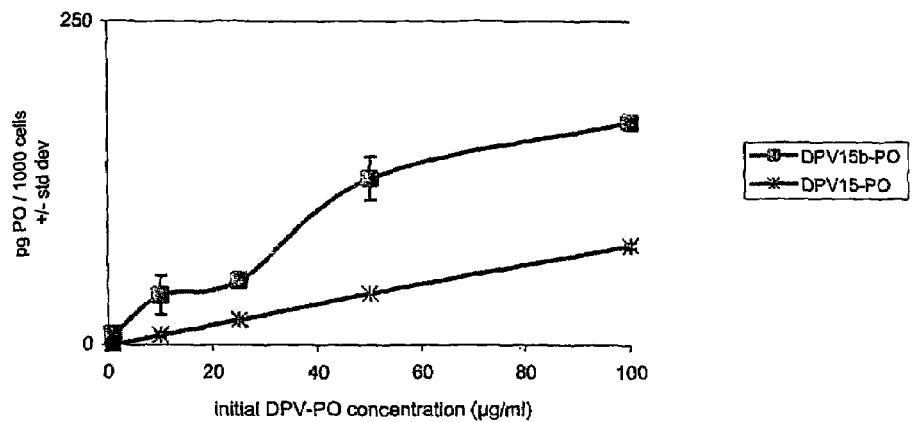
FIG. 8 shows internalization of DPV-PO conjugates as a function of the initial conjugate concentration.

FIG. 8 shows internalization of DPV-PO conjugates as a function of the initial conjugate concentration. HeLa cells cultivated on glass labtek slides for 24 hours were incubated for 4 hours in the presence of DPV-PO conjugates at the initial concentrations indicated on the figure. Internalized PO was quantified after extensive treatment with trypsin to eliminate surface bound material, and subsequent cell lysis. Results are given in picogram PO per 1000 cells.

All subsequent experiments were realized with an initial DPV-PO concentration of 25 μg/ml.

2.4) Influence of the Temperature on the Internalization of DPV-PO Conjugates.

In order to determine if the internalization of DPV-PO conjugates was an energy-dependent phenomenon, we performed quantitative experiments at either 37 or 4° C.

Figure 9:
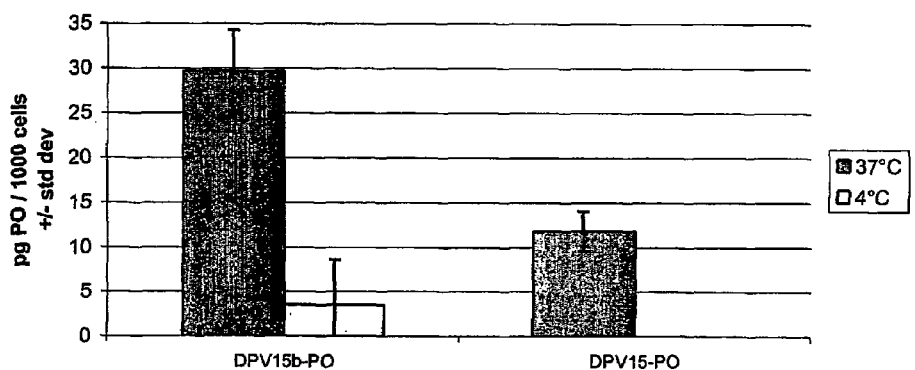
FIG. 9 shows influence of the temperature on the level of internalization of DPV-PO conjugates.

FIG. 9 shows influence of the temperature on the level of internalization of DPV-PO conjugates. HeLa cells cultivated on glass labtek slides for 24 hours were incubated for 4 hours in the presence of DPV-PO conjugates at an initial concentration of 25 μg/ml, at either 37 or 4° C. Internalized PO was quantified after extensive treatment with trypsin to eliminate surface bound material, and subsequent cell lysis. Results are given in picogram PO per 1000 cells.

As seen in FIG. 9, internalization of DPV-PO conjugates is inhibited at 4° C., suggesting an active endocytosis phenomenon.

2.5) Influence of the Cell Surface Glycosaminoglycans (GAGs) on the Internalization of DPV-PO Conjugates.

DPVs originate from human heparin-binding proteins and consequently bind to heparin in vitro. In order to verify that a step of GAGs-binding was necessary in vivo, we performed internalization experiments in both CHO-K1 and PgsA-745 cells, which is a clone of CHO devoid of xylosyltransferase and thus does not produce detectable levels of proteoglycans (Esko et al., 1985; Rostand and Esko, 1997).

Figure 10:
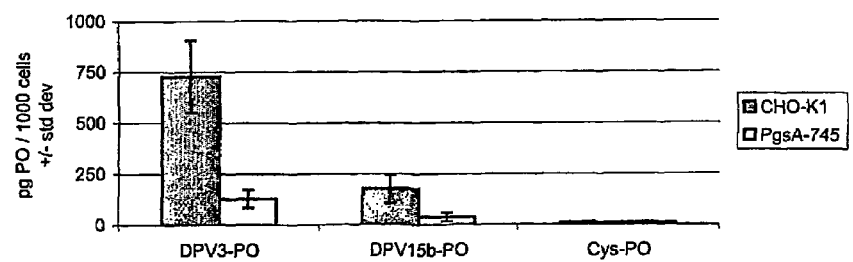
FIG. 10 represents comparative levels of internalization of DPV15b-PO and Cys-PO in CHO and PgsA-745 cells.

FIG. 10 represents comparative levels of internalization of DPV15b-PO and Cys-PO in CHO and PgsA-745 cells. CHO-K1 or PgsA-745 cells cultivated on glass labtek slides for 24 hours were incubated for 4 hours at 37° C. in the presence of DPV-PO conjugates at an initial concentration of 25 µg/ml. Internalized PO was quantified after extensive treatment with trypsin to eliminate surface bound material, and subsequent cell lysis. Results are given in picogram PO per 1000 cells.

Comparison of the level of conjugates internalization in CHO-K1 cells and PgsA-745 cells (FIG. 10) shows that the absence of proteoglycans at the surface of PgsA-745 cells leads to an important decrease of the level of internalized conjugates, thus confirming the binding to GAGs as a first step in DPV-PO internalization.

2.6) Heparin Inhibition of the Internalization of DPV-PO Conjugates.

In order to confirm the binding of DPVs to GAGs as a prerequisite for the internalization of the conjugates, we realized internalization experiments in the presence of heparin in the incubation medium. Heparin should bind to the DPV, and prevent its binding to the cell surface and subsequent internalization.

Figure 11:
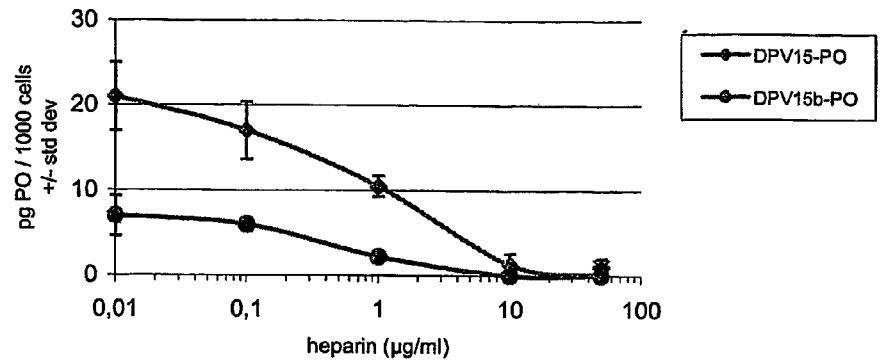
FIG. 11 shows inhibitory effect of heparin on the intracellular accumulation of DPV-PO conjugates.

FIG. 11 shows inhibitory effect of heparin on the intracellular accumulation of DPV-PO conjugates. HeLa cells cultivated on glass labtek slides for 24 hours were pre-incubated with the indicated concentrations of heparin for 1 hour at 37° C. Cells were then incubated for 4 hours in the presence of DPV-PO conjugates at 25 µg/ml in cell culture medium containing the same quantity of heparin. Internalized PO was quantified after extensive treatment with trypsin to eliminate surface bound material, and subsequent cell lysis. Results are given in picogram PO per 1000 cells.

As seen in FIG. 11, incubation of the conjugates in the presence of heparin inhibits its internalization in HeLa cells, thus confirming the interaction between GAGs and DPVs.

2.7) Poly-L-Lys Inhibition of the Internalization of DPV-PO Conjugates.

The inhibition of DPV-PO internalization in cells presenting defects in glycosaminoglycan synthesis (PgsA-745 cells compared to CHO-K1 cells), as well as the inhibition of internalization of DPV-conjugates in the presence of Heparin in the cell culture medium show that cell-associated heparan-sulfate proteoglycans function as cell surface binding sites for extracellular DPV internalization.

In order to verify this hypothesis, we tested the inhibition of DPV-PO internalization in HeLa cells in the presence of Poly-L-Lysine in the incubation medium: positively charged poly-L-Lys should bind to the negative charges of the cell surface, and prevent the binding of DPVs.

Figure 12:
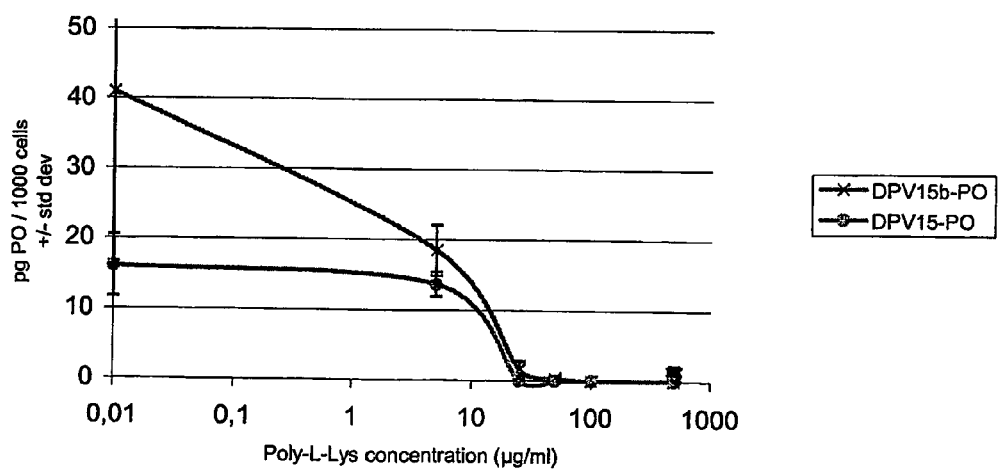
FIG. 12 shows inhibitory effect of Poly-L-Lys on the intracellular accumulation of DPV-PO conjugates.

FIG. 12 shows inhibitory effect of Poly-L-Lys on the intracellular accumulation of DPV-PO conjugates. HeLa cells cultivated on glass labtek slides for 24 hours were pre-incubated with the indicated concentrations of poly-L-Lys for 1 hour at 37° C. Cells were then incubated for 4 hours in the presence of DPV-PO conjugates at 25 µg/ml in cell culture medium containing the same quantity of poly-L-Lys. Internalized PO was quantified after extensive treatment with trypsin to eliminate surface bound material, and subsequent cell lysis. Results are given in picogram PO per 1000 cells.

As seen in FIG. 12, there is a strong inhibition of DPV-PO internalization. The $IC_{50}$ (concentration at which 50% of the maximum internalization is achieved) is situated around 25 µg/ml poly-L-Lys in HeLa cells.

These experiments show that a masking of the negative charges that are present around the cells is sufficient to inhibit DPV internalization, when it is conjugated to peroxidase.

Example 2

Internealization of Control Molecule without Biological Effect (Antibody Anti-Peroxidase)

1) Materials and Methods.
1.1) Nature of the Ligand.
Anti-Peroxidase Immunoglobulin (AntiPO-IgG) was chosen to represent the capacity of DPV15 and DPV15b to internalize very high molecular weight proteins (150 000 Da).

Monoclonal anti-PO antibodies purified from ascite liquid by chromatography on protein G-Sepharose columns: 2 mg/mL in buffer phosphate 0.1M pH 7.4. (origin: Diatos-TT).

Crosslinker: Succinimidyl 4-(N-maleimidomethyl) cyclohexane-1-carboxylate (SMCC, Pierce)

Peptide Vectors: DPV15, DPV15b.

Vivaspin (Vivascience): ultrafiltration membrane (cutoff threshold=10000 or 30000 daltons) for concentration and purification of IgG and the elimination of excess reagents.

Solutions and buffers:
Phosphate 0.1M pH 7.4 (potassium phosphate)
Dimethyl formamide (DMF)
Conjugation buffer: 0.5M NaCl
10 mM Sodium phosphate } pH 7
5 mM EDTA
NaCl 0.15M
NaCl 0.5M 1.2) Conjugation Protocol.
The conjugation method involves four-steps:
Activation of IgG with the crosslinker (SMCC, Pierce)
Filtration of activated IgG on Vivaspin
Conjugation with DIATOS peptide
Elimination of free peptide
a) SMCC Activation of the Immunoglobulin.
Dissolve 2 mg IgG in 1 mL of phosphate buffer 0.1M pH 7.4
Dissolve 200 µg of SMCC in 20 µL of Dimethylformamide (DMF)
Add 11.1 µL of SMCC to the IgG solution (ratio: 25 SMCC/IgG)
Mix and incubate for 30-40 min at room temperature
b) Filtration of the Activated IgG.
Add 1-2 mL of conjugation buffer into the activated IgG preparation and centrifuge in Vivaspin 10-15 min, 3300 g, 20° C.
Add 2 mL of conjugation buffer.
Centrifuge again and repeat this step twice.
c) Conjugation with Peptide.
Dissolve 600 µg of DIATOS peptide in 60 µL of the conjugation buffer.

Add 54.5 µL of DIATOS peptide to IgG-SMCC (Ratio: 12 pept/IgG-SMCC).

Mix and incubate 3 hours at room temperature.

d) Elimination of Uncoupled Peptide and Excess Reagents.

Add 1 mL of 0.5M NaCl into the conjugated IgG preparation.

Concentrate IgG-SMCC-peptide in Vivaspin. Centrifugation 10-15 min, 3300 g, 20° C.

Add 2 mL of 0.15 M NaCl and concentrate the conjugate again.

Repeat this last step one time.

A control was made which consists of AntiPO IgG linked to Cystein.

1.3) Conservation of the Conjugates.

DPV-AntiPO IgG are kept in 100 µl frozen aliquots, diluted in 0.15 M NaCl.

1.4) Characterization of the Conjugated Compounds.

a) SDS-PAGE.

12 µg of each sample are loaded on a 10% acrylamide SDS-PAGE gel.

Migration 100 V—1 h.

Staining of the gel with brilliant blue coomassie solution for 1 hour.

Destraining for 1 hour in $H_2O$/Ethanol/Acetic acid (6V/3V/1V).

Figure 13:
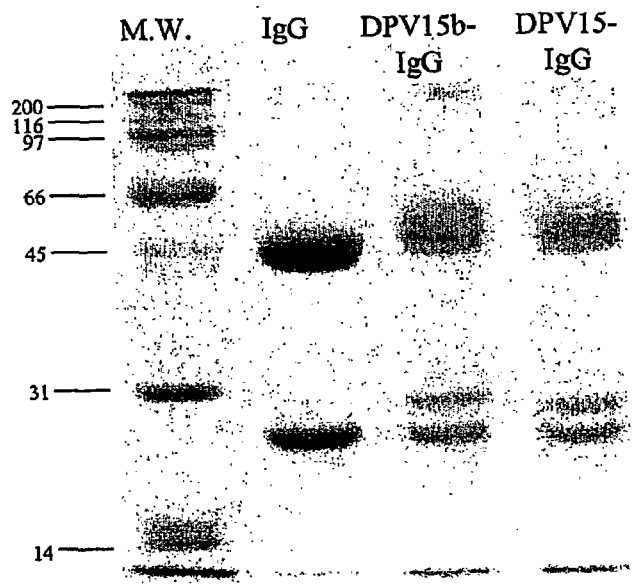
FIG. 13 shows example of SDS-PAGE separation of the DPV-Anti PO IgG conjugates.

FIG. 13 shows example of SDS-PAGE separation of the DPV-Anti PO IgG conjugates. Approximately 12 µg of each conjugate was loaded on a 10% SDS-PAGE gel before migration at 100 V, and subsequent coomassie blue staining.

Lane 1: Molecular Weight standard

Lane 2: AntiPO IgG

Lane 3: DPV 15-AntiPO IgG conjugate.

Lane 4: DPV 15b-AntiPO IgG conjugate.

FIG. 13 shows an increase of molecular weight after coupling, for both heavy and light chains of the IgG. The 25 kDa band in lane 2 (light chain of the IgG) is lower than the bands in lanes 3 and 4. The presence of several bands between 25 and 30 kDa in lanes 3 and 4 is an indication of a heterogeneous coupling. The band corresponding to the heavy chain of the IgG (50 kDa band in lane 2) is also higher in lanes 3 and 4, indicating a coupling of the DPV on both chains of the IgG.

The important heterogeneity of conjugation does not allow the exact determination of the number of conjugated DPVs per IgG molecule by SDS-PAGE analysis.

b) ELISA Test on Heparin Coated Plates.

DPV-AntiPO conjugates and controls (free AntiPO IgG and Cys-AntiPO IgG) are loaded on an ELISA plate previously coated with 5 µg/ml heparin (so that only conjugated compounds will bind and react with PO).

Samples are diluted to a final 10 µg/ml concentration in PBS-Tween. Subsequent_dilutions are then performed.

Conjugates are incubated on the plate for 1 h at 37° C., and washed 3 times in PBS-Tween.

PO is incubated at 1 µg/ml for 1 hour at 37° C. in every well, then washed 5 times in PBS containing 0.1% Tween.

PO substrate is then added (1 pill of 5 mg OPD (Sigma)+10 ml citrate/citric acid buffer 0.1M, pH5.5+100 µl $H_2O_2$ 3%)

Reaction is stopped with 50 µl $H_2SO_4$ 2N after 5 min.

OD is read at 490 nm.

This test allows the verification of the presence of DPVs on the IgG molecules. Nevertheless, the affinity of each DPV for heparin being different, it does not allow quantification of the compounds in solution. This quantification is made by measuring $OD_{280}$, knowing that 1.4 OD unit=1 mg/ml conjugate.

1.5) Internalization Protocols.

Internalization experiments were realized in both HCT116 (colorectal carcinoma) and HeLa (cervical adenocarcinoma) cell lines. Intracellular accumulation was evaluated at a single time point (4 hours).

a) Quantitative Assay.

Cells were routinely seeded at Day 0: $3.6.10^4$ cells/cm$^2$ for HeLa cells, or $7.10^4$ cells/cm$^2$ for HCT116 cells, in 2 wells labtek glass slides (4 cm$^2$/well). Penetration studies were performed at Day 1.

Protocol:

Dilute conjugates in DMEM+10% SVF at 100 µg/ml.

Take culture medium off the cells

Incubate conjugates for 4 hours, 37° C., 5% $CO_2$—400 µl/well (i.e. 40 µg/well)—2 wells per conjugate.

Rinse cells 3 times in PBS.

Incubate the cells in 200 µl Trypsin-EDTA for 30 min at 37° C.

Resuspend cells in 400 µl of complete culture medium.

Count cells.

Centrifuge and rinse cells twice in ice cold PBS.

Resuspend in 220 µl cold lysate buffer (0.1M Tris pH8, 0.5% NP40).

Incubate 15 min at 4° C.

Centrifuge cell lysates.

Distribute cell lysates in a 96 wells plate that was previously coated with anti mouse IgG (twice 100 µl). Prepare a standard curve for antiPO IgG from 10 ng/ml.

Dilute cell lysates_in PBS-Tween and prepare a standard curve for anti PO IgG at 10 ng/ml.

Incubate 1 h at 37° C., and overnight at 4° C.

Rinse 3 times in PBS-Tween.

Incubate Peroxidase 1 µg/ml in PBS-Tween, for 1 h at 37° C.

Rinse 3 times in PBS-Tween.

Add peroxidase substrate (1 pill OPD+10 ml citrate-citric acid buffer 0.1 M, pH5.5+100 µl 3% $H_2O_2$)

Stop the reaction after 9 min by adding 50 µl $H_2SO_4$ 2 N.

Read absorbance at 490 nm and compare to the values of the standard curve.

b) Qualitative Evaluation of the Internalization of DPV-antiPO IgG Conjugates.

PO-Peroxidase Substrate Staining

Cells were routinely seeded at Day 0: $3.6.10^4$ cells/cm$^2$ for HeLa cells, or $7.10^4$ cells/cm$^2$ for HCT116 cells, in 8 wells labtek glass slides (0.7 cm$^2$/well). Penetration studies were performed at Day 1.

Protocol:

Dilute conjugates in complete culture medium at 100 µg/ml.

Take culture medium off the cells

Incubate conjugates for 4 hours, 37° C., 5% $CO_2$—100 µl/well (i.e. 10 µg/well).

Rinse cells 3 times in PBS.

Fix in cold Ethanol for 5 min at −20° C.

Rinse in PBS at RT.

Add PO (10 µg/ml in complete culture medium) 1 h at room temperature.

Rinse 3 times in PBS.

Add peroxidase substrate (di-aminobenzidine, 1 tablet in 10 ml $H_2O$+330 µl $H_2O_2$ 3%)

Rinse 3× in PBS.

Take pictures

TRITC-Conjugated Anti Mouse IgG Staining.

Cells were routinely seeded at Day 0: $3.6.10^4$ cells/cm2 for HeLa cells, or $7.10^4$ cells/cm_ for HCT116 cells, in 8 wells labtek glass slides (0.7 cm_/well). Penetration studies were performed at Day 1.

Protocol:

Dilute conjugates in complete culture medium at 100 µg/ml.

Take culture medium off the cells Incubate conjugates for 4 hours, 37° C., 5% $CO_2$—100 µl/well (i.e. 10 µg/well).

Rinse cells 3 times in PBS.

Fix in cold Methanol/Acetone (1/1) for 5 min at −20° C.

Rinse in PBS at RT.

Block in PBS+5% Donkey serum (sol A) for 30 min at RT.

Incubate with TRITC-conjugated anti mouse 7 µg/ml in sol. A—30 min in the dark at RT.

Rinse in sol A, then in PBS.

Equilibrate in equilibration buffer, and mount in Slow Fade Light Antifade Kit with DAPI (Molecular probes S-24636).

2) Results.

2.1) Quantitative Penetration.

Figure 14:
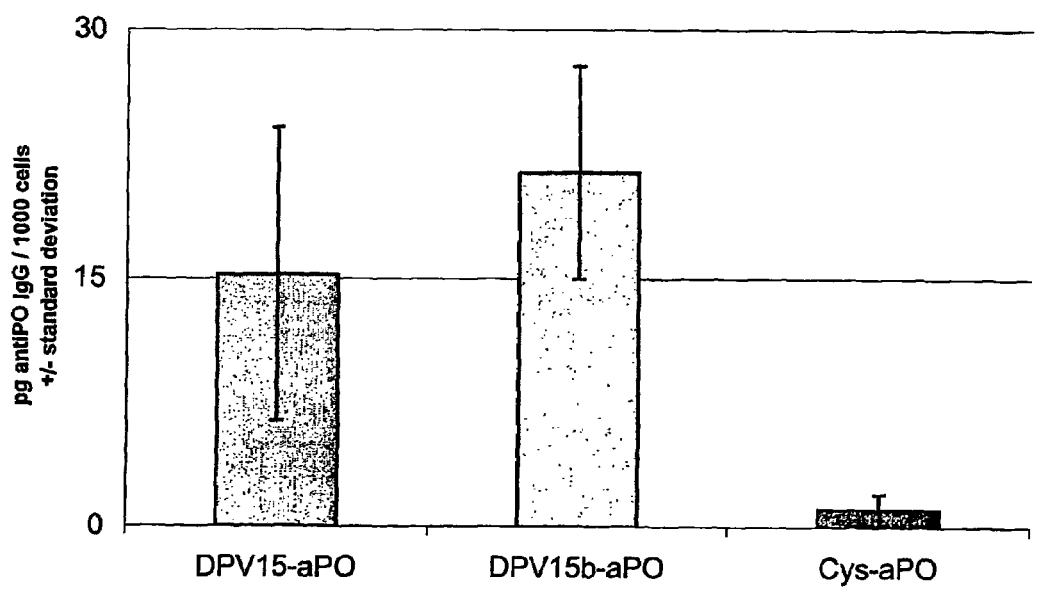
FIG. 14 shows quantitative penetration of the DPV-AntiPO IgG conjugates in HCT116 cells.

FIG. 14 shows quantitative penetration of the DPV-AntiPO IgG conjugates in HCT116 cells. Cell lysis was performed after 4 hours of incubation at an initial DPV-AntiPO IgG conjugates concentration of 100 µg/ml. Results are given as the mean value obtained in three independent experiments, all realized in duplicates.

Table 4 represents net quantities of DPV-antiPO IgG conjugates internalized in HCT116 cells. Results are given in picograms PO/1000 cells, as the mean of three independent experiments.

TABLE 4

|  | pg PO/1000 cells | standard deviation |
| --- | --- | --- |
| DPV15-aPO | 15.2 | 8.9 |
| DPV15b-aPO | 21.4 | 6.4 |
| Cys-aPO | 1.1 | 0.9 |

Figure 15:
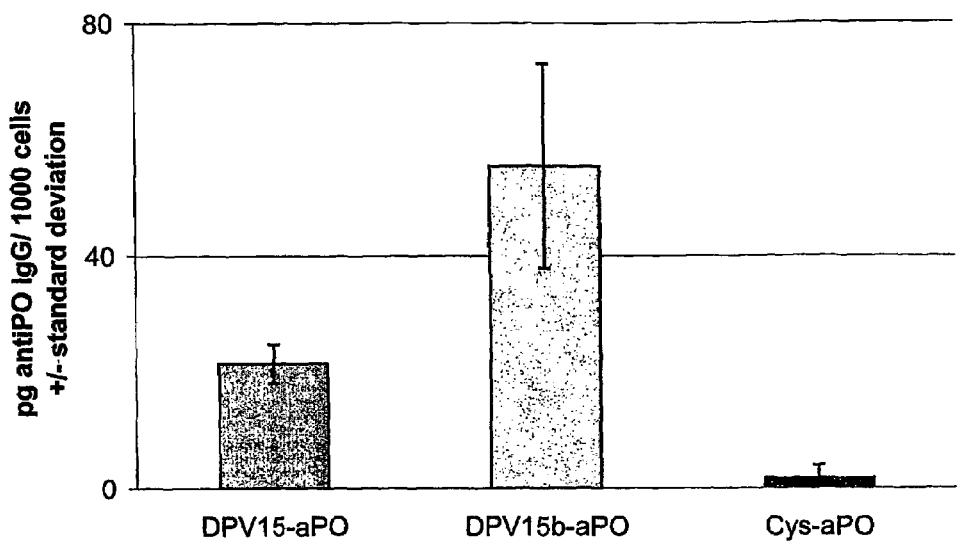
FIG. 15 shows quantitative penetration of the DPV-antiPO IgG conjugates in HeLa cells.

FIG. 15 shows quantitative penetration of the DPV-antiPO IgG conjugates in HeLa cells. Cells were incubated for 4 hours in the presence of the conjugates at an initial concentration of 100 µg/ml. Results are given as the mean value obtained in three independent experiments, all realized in duplicates.

Table 5 represents net quantities of DPV-antiPO conjugates internalized in HeLa cells. Results are given as the mean value of three independent experiments, in picograms PO/1000 cells.

TABLE 5

|  | pg PO/1000 cells | standard deviation |
| --- | --- | --- |
| DPV15-aPO | 21.5 | 3.4 |
| DPV15b-aPO | 55.5 | 17.6 |
| Cys-aPO | 1.7 | 2.2 |

Figure 16:
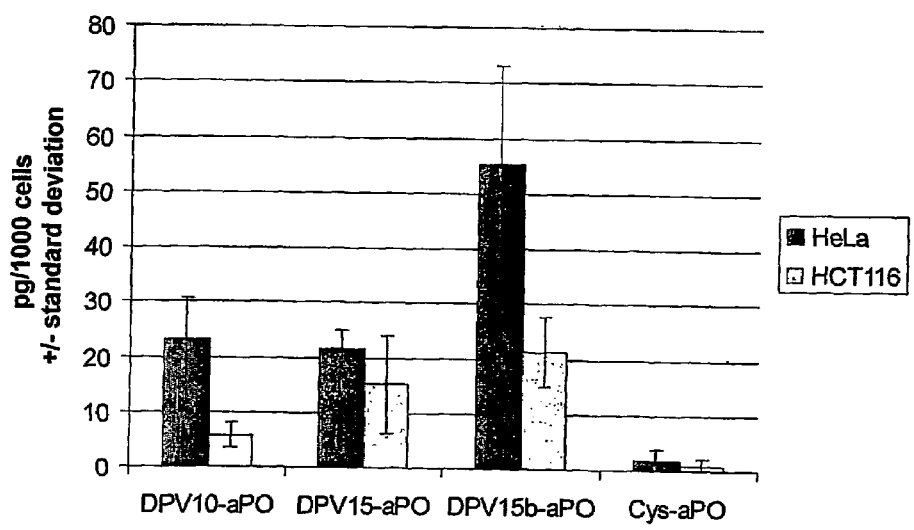
FIG. 16 represent a comparison of the level of internalization of the DPV15-antiPO, DPV15b-antiPO and DPV10-antiPO conjugates in HeLa and HCT116 cells.

FIG. 16 represent a comparison of the level of internalization of the DPV-antiPO conjugates in HeLa and HCT116 cells. The level of internalization depends both on the cell line, and on the DPV.

Table 6 represents number of conjugate molecules internalized in each cell type (million conjugate molecules per cell).

TABLE 6

|  | HeLa millions mol/cell | HCT116 millions mol/cell |
| --- | --- | --- |
| DPV15-aPO | 0.09 | 0.06 |
| DPV15b-aPO | 0.22 | 0.08 |

2.2) Qualitative Evaluation of the Internalization of DPVs-antiPO IgG.

DPV-AntiPO conjugates were incubated with HeLa cells grown on glass labtek slides (4 hours incubation of a 100 µg/ml solution in cell culture medium, at 37° C.). The experiment was realized with the same peptide-AntiPO IgG conjugates as the ones used in the quantitative experiments described above.

Figure 17:
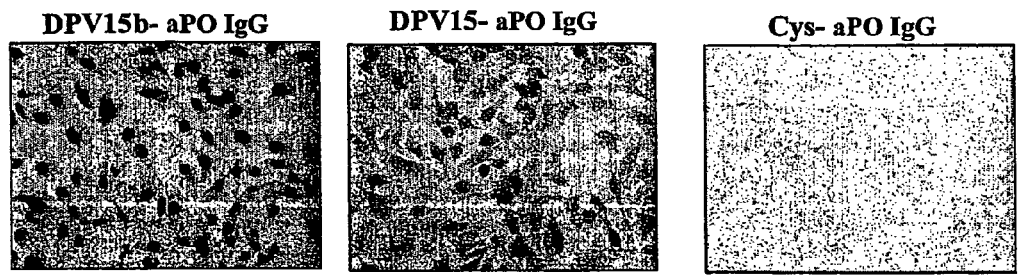
FIG. 17 shows localization of DPV15-antiPO IgG and DPV15b-antiPO IgG conjugates in HeLa cells.
Figure 18:
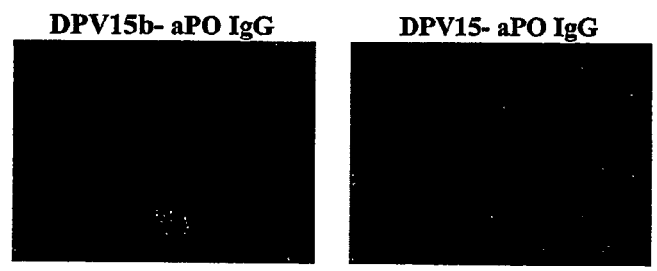
FIG. 18 shows immunofluorescent staining of DPV15-antiPO IgG and DPV15b-antiPO IgG conjugates after internalization in HeLa cells for 4 hours at 37° C.

As shown in FIGS. 17 to 18, in HeLa cells, intracellular localization of PV15b- and DPV15-antiPO IgG conjugates is mainly localized in the nucleus of the cells (weak staining of the cytoplasm, corresponding partly to the quantity of conjugates still in transit between the membrane and the nucleus of the cells, and partly to the proportion of conjugate which final localization would be cytoplasmic).

FIG. 17 shows localization of DPV15-antiPO IgG and DPV15b-antiPO IgG conjugates in HeLa cells. DPV-antiPO IgG conjugates were incubated for 4 hours at an initial concentration of 100 µg/ml on HeLa cells, on 8 wells labtek glass slides. Revelation of the conjugate was performed using peroxidase visualized by its substrate: di-aminobenzidine. Pictures were taken with a Nikon coolpix numeric camera, maximum zoom, after visualization on a Leica microscope (20× lens+0.63× adaptator). The fact that the DPV-antiPO IgG still recognize its antigen (namely Peroxidase) shows that this IgG is still active once coupled to the DPV and internalized inside the cell.

FIG. 18 shows details of HeLa cells after DPV15b-antiPO IgG and DPV15-antiPO internalization. The internalization of the conjugates and the acquisition of the image were realized in the same conditions as for FIG. 17. Enlargement was performed in a second step.

FIG. 18 shows immunofluorescent staining of DPV15-antiPO IgG and DPV15b-antiPO IgG conjugates after internalization in HeLa cells for 4 hours at 37° C. DPV-antiPO IgG conjugates were incubated for 4 hours at an initial concentration of 100 µg/ml on HeLa cells, on 8 wells labtek glass slides. Revelation of the IgG was performed using an anti mouse TRITC-conjugated antibody.

Figure 19:
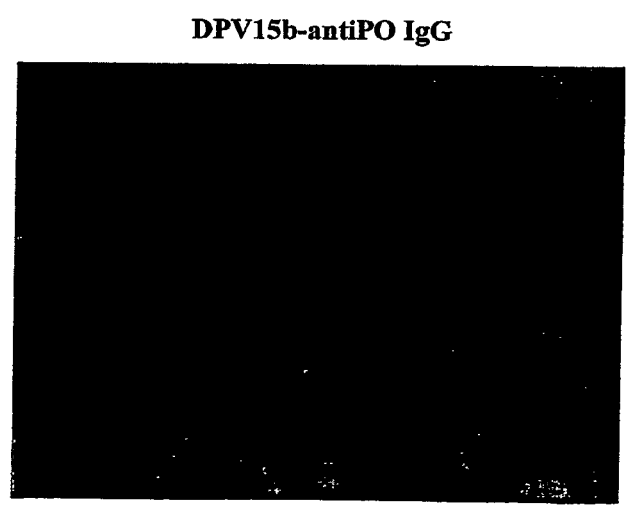
FIG. 19 shows immunofluorescent staining of DPV15b-antiPO IgG conjugates after internalization in HCT116 cells for 4 hours at 37° C. It shows the intracellular localization of DPV15b-IgG conjugates in HCT116 cells.

FIG. 19 shows immunofluorescent staining of DPV15b-antiPO IgG conjugates after internalization in HCT116 cells for 4 hours at 37° C. DPV-antiPO IgG conjugates were incubated for 4 hours at an initial concentration of 100 µg/ml on HCT116 cells, on 8 wells labtek glass slides. Revelation of the IgG was performed using an anti mouse TRITC-conjugated antibody.

FIG. 19 shows the intracellular localization of DPV15b-IgG conjugates in HCT116 cells. The final intracellular localization of the two conjugates was similar in HeLa and HCT116 cells.

Example 3

Internalization of Control Molecule without Biological Effect (Tetra-Methyl-Rhodamine "TMR")

1) Materials and Methods.

1.1) Nature of the Ligand.

Tetra-Methyl-Rhodamine was chosen to represent the capacity of the DPV15 and DPV15b to internalise a small molecule (500 Daltons).

Tetramethylrhodamine-5-maleimide. (Molecular Probes T-6027)

1.2) Conjugation Protocol.

Dissolve 5 mg of TMR-5-maleimide in 207.7 µl of Dimethylformamid (DMF) (final concentration 50 mM)

Dissolve 30 mg of DPV15b or 15.4 mg of DPV15 in 700 µl of DMF (final concentration 10 mM)

Mix 200 µl of TMR solution and 700 µl of DPV solution and incubate 2 hours at room temperature in dark Ad 2 ml $H_2O$ and 8 ml Dichloromethane (DCM).

Mix and centrifuge 2 minutes at 3000 g.

Take aqueous phase (upper phase)

Repeat step 4 to 6 twice.

1.3) Conservation of the Conjugate.

DPV-TMR conjugates are kept as dry powder at −20° C. or 4° C. under argon.

1.4) Internalization Protocol.

a) Quantitative Assay.

Cells were routinely seeded at Day 0: $1.10^5$ cells/cm² for HeLa cells, or $2.10^5$ cells/cm² for HCT116 cells, in 2 well labtek glass slides (4 cm²/well). Penetration studies were performed at Day 1.

Protocol:

Dilute conjugates in complete culture medium (+10% SVF) at 20 µM

Take culture medium off the cells

Incubate conjugates for 2 hours, 37° C., 5% $CO_2$—600 µl/well

Rinse 2 times in complete culture medium and 2 times in PBS

Incubate the cells in 400 µl Trypsin-EDTA for 30 min at 37° C.

Resuspend cells in 600 µl of complete culture medium (+10% SVF)

Count cells

Centrifuge and rinse cells twice in PBS

Resuspend in 1 ml cold lysate RIPA buffer

Incubate 30 min at 4° C.

Prepare a standard curve for cystein-TMR at 200 nM

Fluorescence is counted on a BioRad fluorimeter, (excitation 480 nm and emission 590 nm).

b) Qualitative Evaluation of the Internalisation of DPV-TMR Conjugates.

Cells were routinely seeded at Day 0: $1.10^5$ cells/cm² for HeLa cells, or $2.10^5$ cells/cm² for HCT116 cells, in 8 well labtek glass slides (0.7 cm²/well). Penetration studies were performed at Day 1.

Protocol:

Dilute conjugates in complete culture medium (+10% SVF) at 20 µM

Take culture medium off the cells

Incubate conjugates for 2 hours, 37° C., 5% $CO_2$—100 µl/well

Rinse 2 times in complete culture medium and 2 times in PBS

Fix in 4% PFA 20 min at room temperature

Rinse 3 times in PBS

2) Results.

2.1) Quantitative Intracellular Accumulation.

Figure 20:
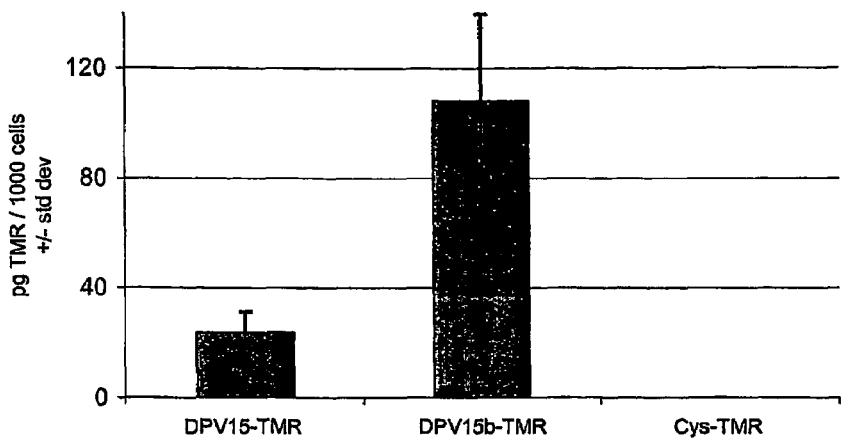
FIG. 20 shows quantitative penetration of the DPV15- and DPV15b-TMR in HeLa cells.

FIG. 20 shows quantitative penetration of the DPV15- and DPV15b-TMR in HeLa cells. Cell lysis was performed after 2 hours of incubation at an initial DPV-TMR conjugates concentration of 20 µM. Results are given as the mean value obtained in two independent experiments.

Table 7 represents net quantities of DPV-TMR conjugates internalized in HeLa cells. Results are given in picograms TMR/1000 cells.

TABLE 7

|  | pg TMR/1000 cells | Standard deviation |
| --- | --- | --- |
| DPV15-TMR | 24 | 8 |
| DPV15b-TMR | 108 | 32 |
| Cys-TMR | 0 | 0 |

Figure 21:
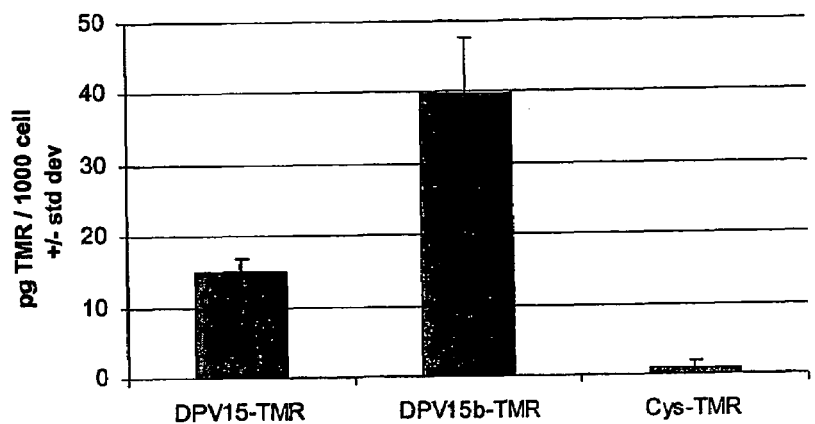
FIG. 21 shows quantitative penetration of the DPV15- and DPV15b-TMR in HCT116 cells.

FIG. 21 shows quantitative penetration of the DPV15- and DPV15b-TMR in HCT116 cells. Cell lysis was performed after 2 hours of incubation at an initial DPV-TMR conjugates concentration of 20 µM. Results are given as the mean value obtained in two independent experiments.

Table 8 represents net quantities of DPV-TMR conjugates internalized in HCT116 cells. Results are given in picograms TMR/1000 cells.

TABLE 8

|  | pg TMR/1000 cells | Standard deviation |
| --- | --- | --- |
| DPV15-TMR | 15 | 2 |
| DPV15b-TMR | 40 | 8 |
| Cys-TMR | 1 | 1 |

Figure 22:
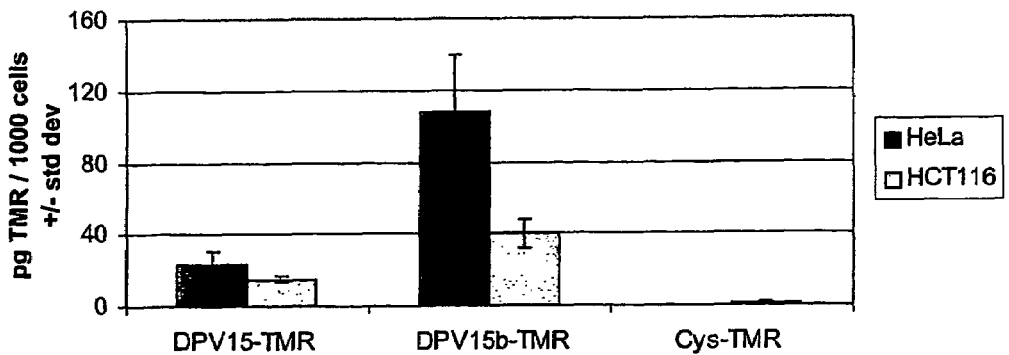
FIG. 22 represents a comparison of the level of internalization of the DPV-TMR in HeLa and HCT116 cells.

FIG. 22 represents a comparison of the level of internalization of the DPV-TMR in HeLa and HCT116 cells.

Table 9 shows an estimated number of conjugated molecules internalized in each type cell type (million conjugate molecules per cells) and ratio of intracellular accumulation of DPV-TMR conjugates in HeLa versus HT116 cells.

TABLE 9

|  | HeLa Millions mol/cell | HCT116 Millions mol/cell | Ratio HeLa/HCT116 |
| --- | --- | --- | --- |
| DPV15-TMR | 28 | 18 | 1.6 |
| DPV15b-TMR | 130 | 47 | 2.8 |

2.2) Qualitative Evaluation of the Internalisation of DPV-TMR in HeLa Cells.

Figure 23:
FIG. 23 shows cytoplasmic punctuate staining of DPV15b-TMR after internalisation in HeLa cells.

FIG. 23 shows cytoplasmic punctuate staining of DPV15b-TMR after internalisation in HeLa cells. Conjugates were incubated with HeLa cells 2 hours at 37° C. at an initial concentration of 20 µM.

Figure 24:
FIG. 24 shows cytoplasmic punctuate staining of DPV15b-TMR after internalisation in HCT116 cells.

FIG. 24 shows cytoplasmic punctuate staining of DPV15b-TMR after internalisation in HCT116 cells. Conjugates were incubated with HCT116 cells 2 hours at 37° C. at an initial concentration of 20 µM. Cell nuclei are stained with DAPI.

2.3) Influence of the Temperature on the Internalization of DPV15b-TMR Conjugates.

Figure 25:
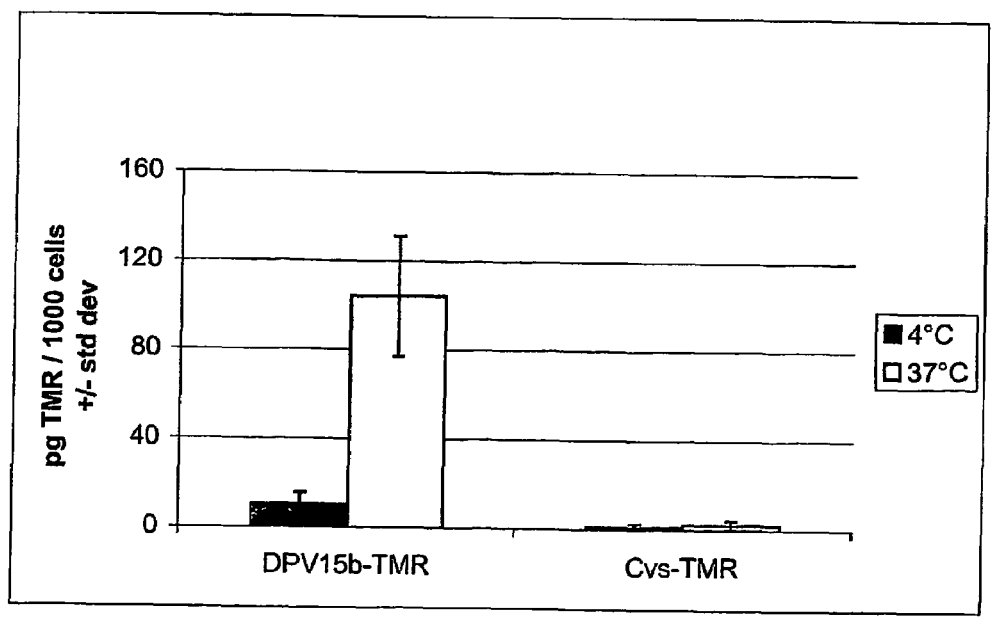
FIG. 25 shows the influence of the temperature on the level of internalisation of DPV15b-TMR conjugates.

FIG. 25 shows the influence of the temperature on the level of internalisation of DPV15b-TMR conjugates. HeLa cells were incubated 2 hours in the presence of DPV15b-TMR conjugates at an initial concentration of 25 µM, at either 37 or 4° C. Cell were then trypsinized before being lysed in RIPA buffer, and fluorescence was quantified. Each value is the result of three independent experiments, each in duplicate.

2.4) Influence of the Cell Glycosaminoglycans on the Internalisation of DPV-TMR Conjugates.

Figure 26:
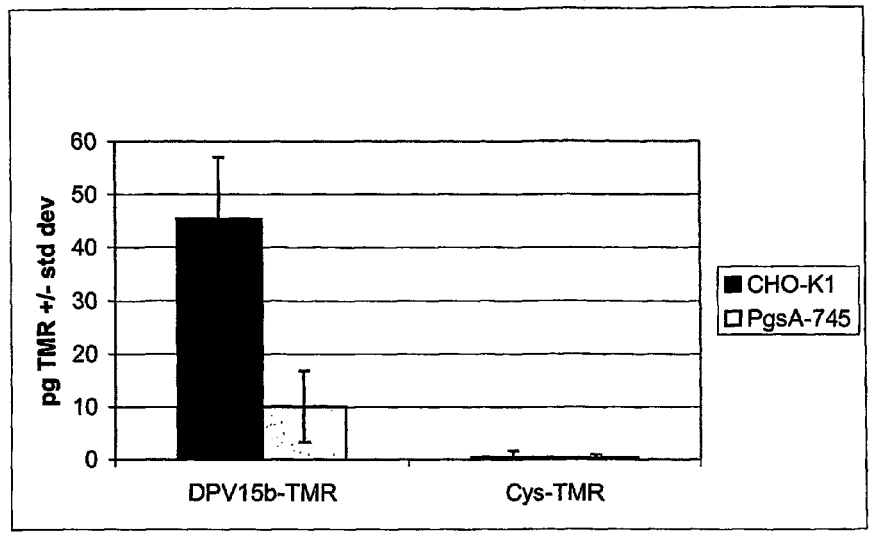
FIG. 26 shows quantification of DPV15b-TMR conjugates internalisation in CHO and PgsA-745 cells.

FIG. 26 shows quantification of DPV15b-TMR conjugates internalisation in CHO-K1 and PgsA-745 cells. Incubation took place for 2 hours at 37° C., before trypsinization and lysis in RIPA buffer for 30 minutes at 4° C. Each value is the result of three independent experiments.

Example 4

Activity of Conjugated Active Molecule (Chlorambucil).

1) Nature of the Ligand.

Figure 27:
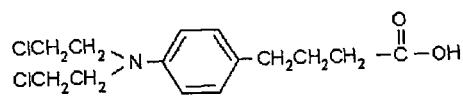
FIG. 27 shows Chlorambucil formula.

Chlorambucil (Chl) is an inhibitor of DNA and RNA synthesis. It is an alkylating agent causing intra- or inter-crosslinks in DNA molecules. Reactive groups are the two Cl⁻ groups. Its formula is given in FIG. 27.

Resistance to chlorambucil has been linked to an increase in (i) the efflux pump MRP1, and (ii) the glutathione S-transferases (GSTs) that are involved in the detoxification of electrophilic toxins (Morrow C S., 1998, *J. Biol. Chem.*, 273: 20114).

In clinic, the major problem is the risk of induction of secondary leukemias following therapy with chlorambucil (Travis L B., 1994, *J. Natl. Cancer Inst.*, 86:1450).

Coupling Peptide Vectors (DPVs) to chlorambucil has 2 advantages:

DPVs overcome multidrug resistant (MDR) phenotype due to expression of membrane efflux pumps such as the P-glycoprotein (P-gp) or the multidrug resistance proteins (MRPs), that can extrude a wide range of anticancer drugs.

DPVs increase solubility of chlorambucil in $H_2O$.

Therefore, DPV-chlorambucil conjugates may be more soluble and more active in resistant tumors.

2) Conjugation.

2.1) Materials.

DPV15-E-Chl conjugate was compared to non-conjugated Chl (Fluka, Cat# 23125).

Chl is not soluble in aqueous solutions but it may be solubilized in ethanol.

For viability assays, Chl was solubilized in ethanol at 50 mM then diluted in culture medium at 1 mM (so the highest concentration tested on cells contained 2% ethanol).

Molar extinction coefficient at 258 nm was calculated for Chl: 17.900±1.200

Exact concentration of Chl and DPV15-E-Chl solutions was calculated after dilution 1/100 in $H_2O$, measurement of $OD_{258\,nm}$ and using the following formula:

[molar concentration]=$OD_{258\,nm}$/17.900

2.2) Conjugation Protocol.

Figure 28:
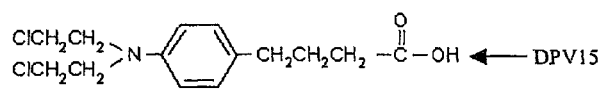
FIGS. 28 and 29 represent Chlorambucil conjugated to DPV15 with an ester link (E) on the OH group.
Figure 29:
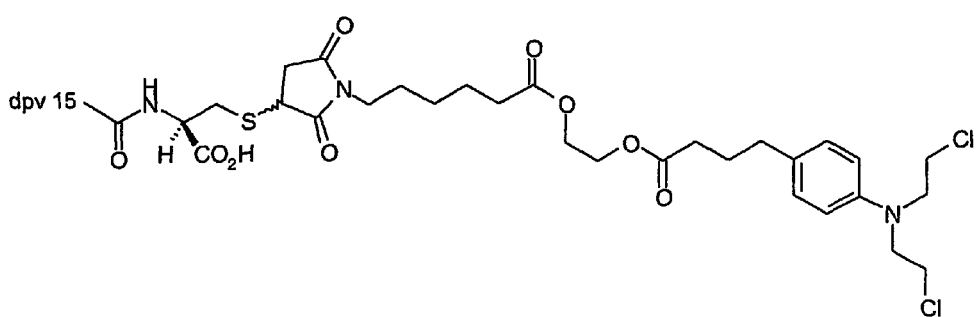

Chlorambucil has been conjugated to DPV15 with an ester link (E) on the $CO_2H$ group as shown on FIGS. 28 and 29. The conjugation has been carried out by Laboratoire de Chimie Bioorganique et de Biologie Moléculaire et Cellulaire (LCBBMC) at Ecole Nationale Supérieure de Chimie de Paris (ENSCP).

The two reactive groups (Cl⁻) are free, therefore the conjugate does not need to be cleaved to be active.

(SEQ ID NO: 11)
DPV15: NH2-LRRERQSRLRRERQSR-Cys-COOH (16 + 1 aa).

nuclear localization (DPV15-PO & DPV15-mAb anti-PO)
DPV15-E-Chlorambucil:

1 batch: Nov. 10, 2001 70 mg (soluble in water at ≧10 mg/ml), molecular weight=2825.15

HPLC purity~90%, net peptide content=60% (counter-ion=TFA)

HPLC analysis showed that preparation contains 90% of DPV15-E-Chl and 10% of "modified" DPV15-E-Chl with a different absorbance spectrum. This modification is not due to proteolysis of the ester link and is most likely due to instability of Chl as previously described (Bosanquet A G., 1986, *Cancer Chemother. Pharmacol.*, 18:176). It could be due to (i) modification of the aromatic nucleus of Chl or (ii) interaction of the 2 Cl⁻ atoms contained in Chl with $H_2O$ molecules. We would have to perform mass spectrometry analysis, in order to identify this component.

After overnight incubation at room temperature and protected from light, both Chl (0.1 mg/ml in $H_2O$+0.1% TFA) and DPV15-E-Chl (0.5 mg/ml in $H_2O$+0.1% TFA) are degraded (50% degradation).

3) Viability Assay.

3.1) Human Cell Lines.

HCT116: human colon carcinoma (origin: ATCC #CCL-247)

HT29: human colon carcinoma, low P-gp expression (origin: ATCC #HTB-38)

K562: human chronic myelogenous leukemia (CML) (origin: ATCC #CCL-243).

3.2) Viability Assay.

Viability assays were performed. Briefly, cells are seeded in 96-well plates and incubated with increasing concentrations of drugs (i) for 1 hour then cells are rinsed and incubated with fresh medium without drugs for 48 hours, or (ii) for 48 hours. A WST-1 test (from Roche) was performed and $IC_{50}$ values (drug concentration that inhibits 50% of cell viability) were estimated from sigmoidal regressions.

4) In Vitro Efficacy.

DPV15-E-Chl conjugate was compared to non-conjugated Chl and 5FUra for the inhibition of in vitro cell proliferation of human carcinoma and leukemia cells. We calculated IC50 values=drug concentration that inhibits 50% of cell viability.

TABLE 10

| $IC_{50}$ values* (μM) | 1 h incubation + 48 h | | | 48 h incubation | | |
|---|---|---|---|---|---|---|
| | 5FUra | Chl | DPV15-E-Chl | 5FUra | Chl | DPV15-E-Chl |
| K562 leukemia | nt | >500 (n = 2) | 30 ± 0 (n = 2) | nt | 250 ± 70 (n = 2) | 30 ± 0 (n = 2) |
| HCT116 colon | 113 ± 40 (n = 3) | 533 ± 251 (n = 3) | 43 ± 15 (n = 3) | 8.5 ± 7.9 (n = 4) | 200 ± 70 (n = 2) | 25 ± 7 (n = 2) |
| HT29 colon | >1000 (n = 2) | 650 ± 495 (n = 2) | 60 ± 0 (n = 2) | 725 ± 388 (n = 2) | 250 ± 70 (n = 2) | 325 ± 176[#] (n = 2) |

Chl was solubilized in ethanol, DPV15-E-Chl and 5FUra were solubilized in water
*mean value from n independent experiments ± standard deviation
nt: not tested
[#]see conclusion 5) Conclusions—Discussion.

5.1) In term of Solubilization.

Conjugation of DPV15 to Chlorambucil led to a water soluble conjugate.

5.2) In Term of Efficacy on Tumor Cell Growth.

in K562 leukemia, DPV15-E-Chl conjugate is much more efficient than Chl ($\geq$16-fold after short exposure, and 8-fold after long exposure).

in HCT116 colon carcinoma, DPV15-E-Chl conjugate is more efficient than Chl (12-fold after short exposure, and 8-fold after long exposure) and as efficient as the drug that is used in clinic for this indication, namely 5FUra.

in HT29 colon carcinoma, resistant to 5FUra, DPV15-E-Chl conjugate is more efficient than Chl after short exposure (11-fold) and is more efficient than 5FUra after short exposure ($\geq$17-fold).

(#: there is no explanation for the unexpected high value obtained after long exposure).

The lack of activity for Chl is not due to the solvent used for solubilization (ethanol) as we obtained the same results for DPV15-E-Chl solubilized in water and in ethanol (data not shown).

Nevertheless, the fact that we did not detect any activity for Chl may be due to the fact that we did not obtain a good solubilization of Chl in ethanol. In literature, an efficacy of Chl has been described in vitro on B-CLL with a median $IC_{50}$ of 40.5 mM (Silber R., 1994, *Blood*, 84:3440).

Example 5

Activity of Conjugated Active Molecule (Paclitaxel)

1) Nature of the Ligand.

Taxanes are cytotoxic agents that inhibit the mitotic spindle during cell division through inhibition of β-tubulin depolymerisation (Nogales E., 1999, *Cell. Mol. Life Sci.* 56:133). The two taxanes in clinical use are paclitaxel (Taxol®) and docetaxel (Taxotere®). Paclitaxel was extracted in the late 1960s from the bark of the Pacific Yew, *Taxus brevifolia* (Wall M E., 1995, *Cancer Res.* 55:753). Docetaxel was obtained in the mid 1980s as part of a major chemistry effort to develop a semi-synthesis process to obtain paclitaxel and analogs using 10-deacetyl baccatin III, a precursor extracted from the needles of the European Yew treen *Taxus baccata* (Gueritte-Voegelein F., 1991, *J. Med. Chem.*, 34:992).

The mechanims of resistance described most often for paclitaxel is the multidrug-resistance (MDR) phenotype mediated by the 170 kDa P-glycoprotein (P-gp) membrane efflux pump encoded by the mdr1 gene and that can extrude a wide range of anticancer drugs. Overexpression of this transport system is recognized as a relevant mechanism of resistance to Taxol® (Zunino F., 1999, Drug Resist. Updat. 2:351).

Paclitaxel is not soluble in water, and is solubilized in cremophor (polyoxyethylated castor oil) or ethanol. In clinic, administration of paclitaxel is intraveinous and these 2 excipients have been associated with hypersensitivity (HSR) in patients treated with paclitaxel.

Coupling Diatos Peptide Vectors (DPVs) to paclitaxel (PTX) could have 2 advantages:

DPVs could overcome the MDR phenotype due to expression of P-gp.

DPVs may increase water solubility of paclitaxel.

Therefore, DPV-PTX conjugates may be more soluble and more active in resistant tumors.

2) Conjugation.

Paclitaxel (PTX) and DPV were conjugated.

DPV15/DPV3-E-PTX conjugates were compared to:

non-formulated paclitaxel from Hauser (Lot # Tech-6-00600-A)

clinical grade formulated Taxol® from Bristol-Myers Squibb (Lot # 01H25-A).

Paclitaxel is not soluble in aqueous solutions but it may be solubilized in polyoxyethylated castor oil (cremophor EL, Sigma cat#C5135).

For viability assays, paclitaxel was solubilized at 5 mM in water containing 20% cremophor EL, then diluted in culture medium at 500 µM (so the highest concentration tested on cells contained 2% of cremophor EL).

DPV15-E-PTX and DPV3-e-PTX conjugates was supplied by Laboratoire de Chimie Bioorganique et de Biologie Moléculaire et Cellulaire (LCBBMC) at Ecole Nationale Supérieure de Chimie de Paris (ENSCP).

Figure 30:
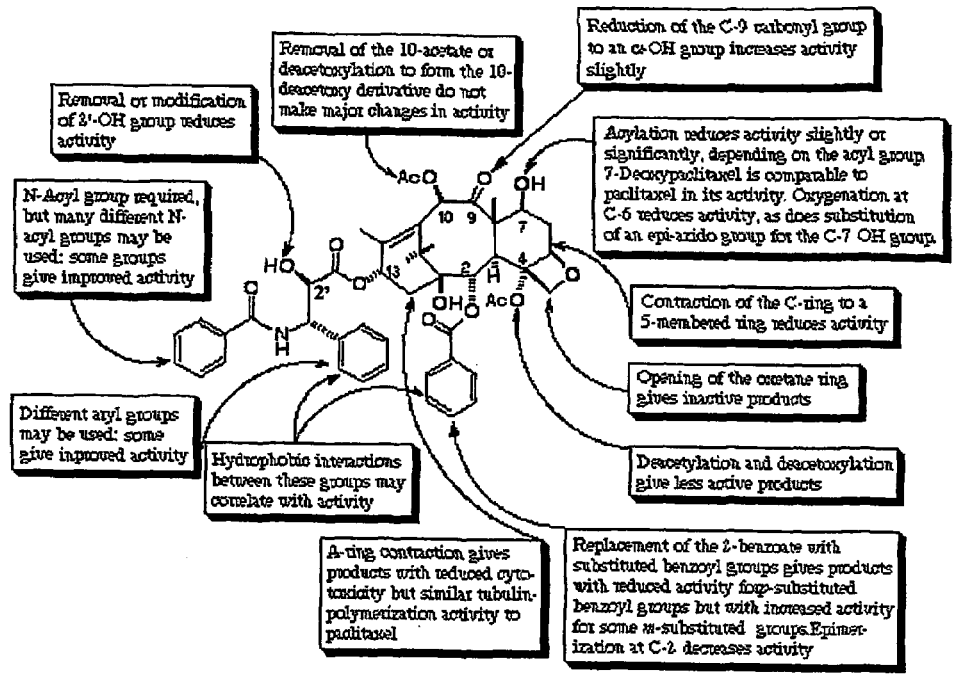
FIG. 30 represents Paclitaxel formula with its reaction sites.
Figure 31:
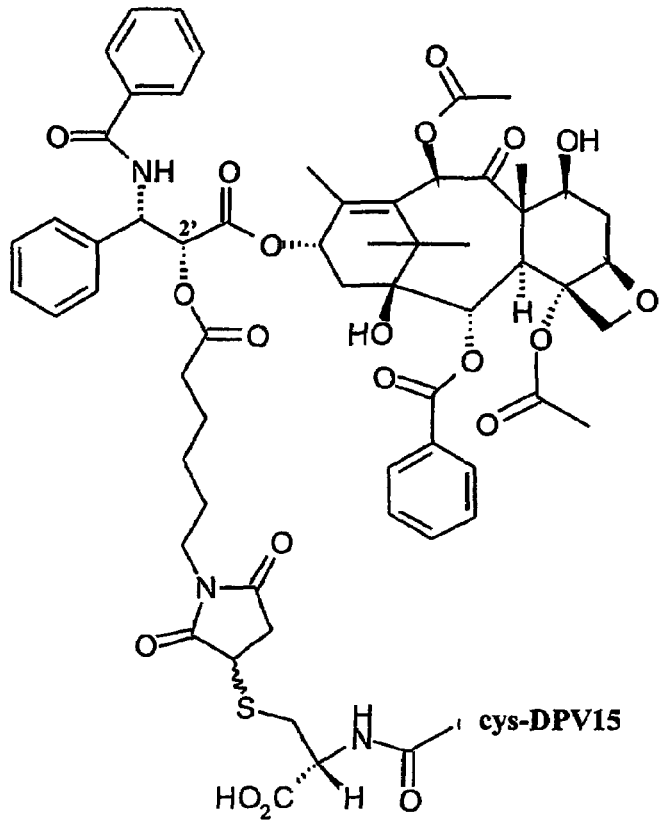
FIG. 31 represents DPV15-E-PTX formula.

Paclitaxel (from Hauser) was conjugated to DPV15 and DPV3 with an ester link (E) on the 2'-OH group. This 2'-OH group is important for paclitaxel activity (see FIGS. 30 and 31). Therefore, DPV-E-PTX conjugates are partially active, they are prodrugs that are fully active after cleavage of the ester link by esterases.

DPV15:                                    (SEQ ID NO: 11)
NH2-LRRERQSRLRRERQSR-Cys-COOH (16 + 1 aa).

Nuclear localization: as reported in study on internalization of DPV-peroxidase conjugates and study on internalization of DPV-antibody anti peroxidase conjugates.

DPV3:                                     (SEQ ID NO: 12)
NH2-RKKRRRESRKKRRRES-Cys-COOH (16 + 1 aa).

Cytoplasmic localization: as reported in study on internalization of DPV-peroxidase conjugates and study on internalization of DPV-antibody anti peroxidase conjugates.

Remark: A cystein (Cys) has been added to the DPV amino acid sequences for conjugation. DPV15-E-PTX(see formula on FIG. 31).

Theoretical molecular weight: 3331.73

Solubility: soluble in water ($\geq$10 mg/ml)

Counter-ion: TFA

2 Lots for DPV15:

DIAT0049 (ALL0050) 55 mg (Jun. 12, 2001) HPLC purity >99%, net peptide content=80%

DIAT0050 (ALL0050bis) 15 mg (Jun. 12, 2001) HPLC purity >99%, net peptide content=88%

DPV3: DIAT0057, HPLC purity >99%

3) Viability Assay.

3.1) Human Cell Lines.

OVCAR-3: human ovary carcinoma (origin: ATCC #HTB-161)

NCI-H1299: human non small cell lung carcinoma (NSCLC) (origin: ATCC #CRL-5803)

MES-SA/Dx5: human uterine sarcoma, resistant to paclitaxel, expressing high P-gp (origin: ATCC #CCL-1977).

3.2) Viability Assay.

Viability assays were performed. Briefly, cells are seeded in 96-well plates and incubated with increasing concentrations of drugs for 1 hour then cells are rinsed and incubated with fresh medium without drugs for 72 hours. A WST-1 test (from Roche) was performed and $IC_{50}$ values (drug concentration that inhibits 50% of cell viability) were estimated from sigmoidal regressions.

4) Results.

DPV15-E-PTX and DPV3-E-PTX conjugates were compared to non-formulated paclitaxel (from Hauser), clinical grade formulated Taxol® (from BMS), Doxorubicin (Dox) and DPV1047-E-Dox conjugate (this conjugate has been described in PCT patent application published under number WO 01/64738; DPV1047 is reported as nuclear localization).

```
DPV1047:                                  (SEQ ID NO: 13)
NH2-Cys-VKRGLKLRHVRPRVTRMDV-COOH (19 + 1 amino
acids) (A cystein (Cys) has been added to the DPV
amino acid sequence for conjugation).
```

We tested the inhibition of in vitro cell proliferation of human carcinoma cells, and we calculated $IC_{50}$ values=drug concentration that inhibits 50% of cell viability.

TABLE 11

| $IC_{50}$ | 1 h incubation + 72 h post-incubation | | | | | |
|---|---|---|---|---|---|---|
| values (μM)* | Dox | Paclitaxel (Hauser) | Taxol® (BMS) | DPV15-E-PTX | DPV3-E-PTX | DPV1047-E-Dox |
| OVCAR-3 ovary carcinoma | 7.3 ± 4.2 (n = 6) | 0.04 ± 0.02 (n = 6) | 0.02 ± 0 (n = 2) | 0.37 ± 0.05 (n = 5) | 0.34 ± 0.19 (n = 5) | 8 ± 2 (n = 2) |
| H1299 NSCLC | 0.62 ± 0.32 (n = 6) | 0.23 ± 0.17 (n = 6) | 0.028 ± 0.004 (n = 2) | 4.3 ± 2.7 (n = 4) | 3.4 ± 2.8 (n = 5) | 0.65 ± 0.28 (n = 2) |
| MES-SA/Dx5 uterine sarcoma | 350 ± 111 (n = 5) | >500 (n = 6) | >500 (n = 2) | 33 ± 5.7 (n = 5) | 16 ± 2.2 (n = 5) | 90 ± 0 (n = 2) |

*mean value from n independent experiments ± standard deviation.

Paclitaxel from Hauser is solubilized in Cremophor EL

Taxol® from BMS is already formulated (in Cremophor EL)

DPV15-E-PTX and DPV3-E-PTX are solubilized in water

The cytotoxicity observed with free paclitaxel (from Hauser) solubilized in cremophor EL was not due to the solvent used for solubilization as we did not observe any cytotoxicity of the solvent alone, at the maximal concentration used (2%) (data not shown).

Comparison between non-formulated paclitaxel from Hauser (solubilized in Cremophor EL) and clinical grade formulated Taxol® from BMS showed the same efficacy (except in H1299 cells where Taxol® was 10-fold more efficient than paclitaxel).

In Term of Solubilization.

Conjugation of DPV15 and DPV3 to paclitaxel with an ester link led to water soluble conjugates.

In Terms of Efficacy on In Vitro Tumor Cell Proliferation.
  in OVCAR-3 ovary carcinoma sensitive to doxorubicin and paclitaxel, both DPV-E-PTX conjugates are less efficient than paclitaxel (9-fold) and more efficient than doxorubicin and DPV1047-E-Dox conjugate (22-fold).
  in H1299 non small cell lung carcinoma sensistive to doxorubicin and paclitaxel, both DPV-E-PTX conjugates are less efficient than paclitaxel (16-fold) and less efficient than doxorubicin and DPV1047-E-Dox conjugate (6-fold).
  in MES-SA/Dx5 uterine sarcoma resistant to doxorubicin and paclitaxel, both DPV-E-PTX conjugates are more efficient than paclitaxel (15- to 31-fold), doxorubicin (10- to 22-fold) and DPV1047-E-Dox conjugate (3- to 5.5-fold).

Example 6

Toxicity Evaluation of DPV15-Amphotericin B Conjugate

1) Nature of the Ligand.

Amphotericin B (AmB), a heptane macrolide produced by *Streptomyces nodosus*, is one of the most potent and effective antibiotics used to combat systemic fungal infections, despite its toxicity. AmB exerts toxic effects on biological membranes by adhering to sterols within cellular membranes. It binds to ergosterol in the fungal cell membrane and to cholesterol in mammalian cells (hence its toxicity) via hydrogen bonds and van der Waals forces.

2) Conjugation

Amphotericin B (AmB) has been conjugated to DPV15 with an ester link.

```
DPV15:                              (SEQ ID NO: 11)
NH2-LRRERQSRLRRERQSR-Cys-COOH
(Cystein has been added for conjugation).
```

To a solution of DPV15 (112 mg) in water (3.4 ml) was added sodium borohydride (12 mg; 0.34 mmol) and the solution was stirred at 22° C. for 20 min. Excess of NaBH was destroyed by addition of acetic (0.037 ml, 0.68 mmmol) The pH of the solution was adjusted to 5.5 adding solid $NaHCO_3$. A solution of Amphotericin B maleimidocaproyl amide (40 mg, 0.034 mmol) in dimethylformamide (1.5 ml) was added drop wise to the reduced peptide and the resulting mixture was stirred at room temperature for 2.5 hours. Purification by HPLC, followed by liophylisation gave the trifluoroacetate salt of DPV15-AmB conjugate.

Figure 32:
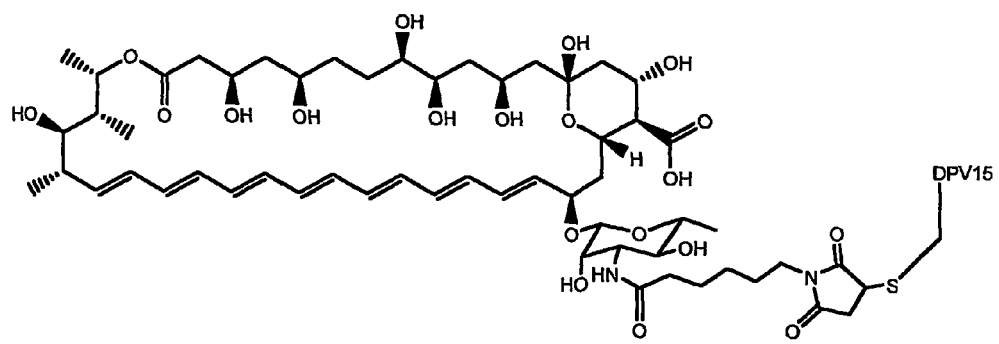
FIG. 32 represents DPV15-Amphotericin B formula

FIG. 32 shows DPV15-AmB conjugate formula.

3) In Vitro Efficacy Assay

In vitro antifungal activity of DPV15-AmB conjugate has been evaluated on four fungus species namely, *Candida parapsilosis* (ATCC 22019), *Candida albicans* (ATCC 90028), *Aspergillus fumigatus* (IP 2001/183.02) and *Cryptococcus neoformans* (NIH 52D) and compared to Amphotericin B and DPV15. $MIC_{80}$ (the lowest drug concentration which reduces strain growth by 80% compared to the drug free control) has been performed in accordance with NCCLS M27A standards (National Committee for Clinical Laboratory Standards, document M27A), using a microtiter modification of the NCCLS M27A standard, in RPMI 1640 buffered with MOPS. This Minimum Inhibitory Concentration has been determined after 48 hours and the incubation temperature was 37° C.

Results:

In vitro activity of DPV15-AmB and comparators against fungus species are reported table 12 below.

TABLE 12

| Strains | MIC (µg/ml) | | |
|---|---|---|---|
| | DPV15-AmB* | AmB* | DPV15 |
| Candida parapsilosis | 0.5 | 0.25 | >8 |
| Candida albicans | 0.5 | 0.5 | >8 |
| Cryptococcus neoformans | 0.25 | 0.06 | >8 |
| Aspergillus fumigatus | 4 | 1 | >8 |

*MIC$_{80}$s are expressed in µg/ml of AmB active product.

As shown in Table 12, the antifungal activity of AmB is maintained after coupling with DPV15. DPV15-AmB conjugate inhibited the growth of Candida strains at a concentration equal to AmB. MIC of DPV15-AmB is increased (x4 factor) against Cryptococcus and Aspergillus in comparison of AmB but the conjugate remains an active product (MIC<8 µg/ml).*

4) In Vivo Antifungal Activity

In vivo antifungal activity of DPV15-AmB conjugate has been evaluated in a lethal murine candidiasis model (AmB-sensitive strain). Mice were inoculated by the intravenous (i.v.) with an LD$_{100}$ (the 100% lethal dose) of Candida albicans (ATCC 90028). Test substances (DPV15-AmB and AmB (Fungizone)) and vehicle control were administrated i.v. with doses ranging from 0.25 mg/kg to 2.5 mg/kg AmB equivalent to test animals 3 hours after the fungal inoculation. Mortality was recorded once daily for 8 days.

Figure 33:
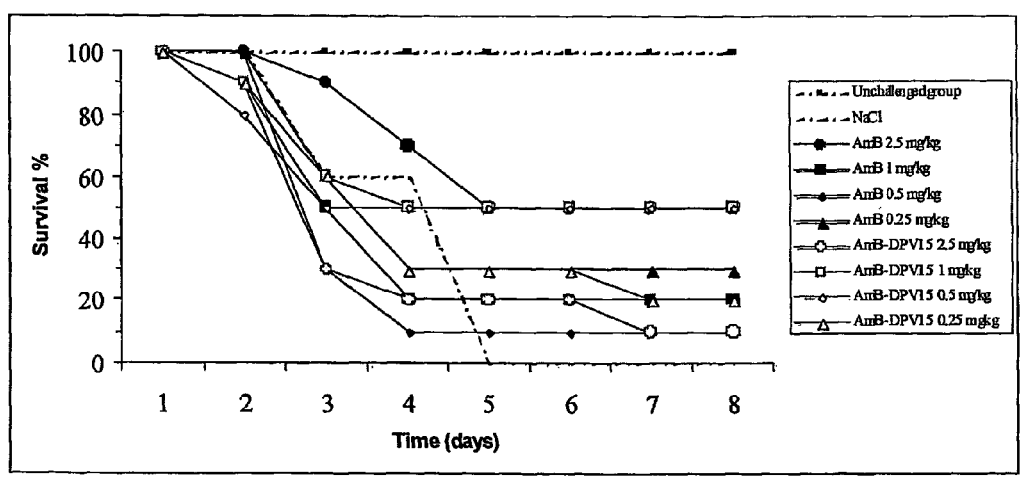
FIG. 33 shows efficacy of DPV15-AmB conjugate in a lethal murine candidiasis model following a single intravenous administration

FIG. 33 shows that none of the treatment regimens resulted in 100% survival. However 1 and 0.5 mg/kg AmB equivalent of DPV15-AmB conjugate (denoted AmB-DPV15 in Figure) gave 50% survival on day 8, as compared to 20% and 10% survival for fungizone same concentrations, respectively. 50% survival was obtained with 2.5 mg/kg AmB (Fungizone) on day 8. The difference in corresponding doses showing a prevention of mortality over a week suggests that DPV15-AmB is active at a lower dose than the reference compound (Fungizone).

5) In Vivo Toxicity Evaluation 5-a) Hemolytic Activity

Conjugation of DPV15 to AmB was shown to greatly enhance the solubility of the molecule. The intra-venous injection being the most favourable one, cytotoxic activity of the conjugate on Human Red Blood Cells has been tested. Tested concentrations were from 0 to 4 µg/ml. Hemolytic activity of conjugate has been compared to AmB and Abelcet™ (lipid formulation of AmB).

Figure 34:
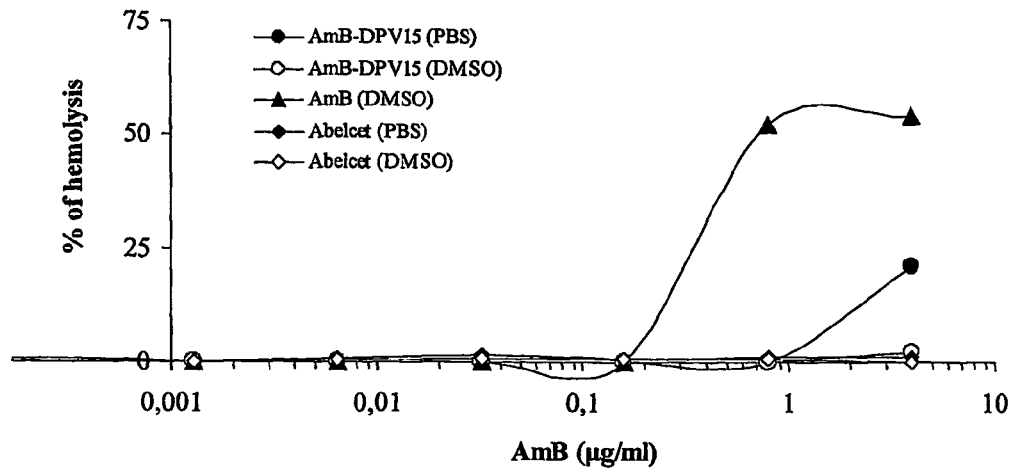
FIG. 34 shows hemolytic activity of DPV15-AmB conjugate, and related molecules

Human red blood cells were incubated in the presence of the various molecules for 1 hour at 37° C. Products were diluted as indicated on the FIG. 34. Percentage of hemolysis is given as the mean of two independent values. FIG. 34 shows an IC$_{50}$ for AmB around 1 µg/ml, which corresponds to the value exposed in the literature (Tabosa Do Egito et al., In-vitro and In-vivo evaluation of a new amphothericin B emulsion-based delivery system. *J Antimicrob Vhemother.* 1996 September; 38(3):485-97). In contrast, 50% of hemolysis is never reached for AmB-DPV15 conjugates (denoted AmB-DPV15 in figure) in the range of concentrations that were tested. Conjugation of AmB to DPV15 peptide lowers its hemolytic activity.

5-b) Single Dose Toxicity

The single dose toxicity of the DPV15-AmB conjugate was assessed by mortality and/or body weight loss after a single dose intravenous injection. Mice were treated with DPV15-AmB 2.57, 3.68, 5.52, 7.36, 9.2, 18.4 and 36.8 mg/kg with vehicle (NaCl/H$_2$O 9/1 v/v). These different doses correspond to 0.7, 1, 1.5, 2, 2.5, 5 and 10 mg/kg of AmB respectively. The dose of 1 mg/kg corresponds to the MTD of AmB exposed in the literature (Tabosa Do Egito et al., In-vitro and In-vivo evaluation of a new amphothericin B emulsion-based delivery system. *J Antimicrob Vhemother.* 1996 September; 38(3):485-97).

Acute lethal toxicity was observed with the greater dose tested (36.8 mg/kg) but no with others.

At Day 28, no effect on the body weight was observed on mice treated with DPV15-AmB at 2.57, 3.68, 5.52, 7.36 and 9.2 mg/kg. For mice injected at 18.4 mg/kg, 1 mouse was found dead in cage 24 hours after the injection. The two other surviving mice lost about 12% of their initial body weight 24 hours after the injection. After Day 15, these mice regained weight. This data suggests that the maximal tolerated dose of DPV15-AmB conjugate is between 18.4 and 9.2 mg/kg (respectively 5 and 2.5 mg/kg AmB equivalent).

Example 7

Use of DPVs for the Intracellular Delivery of $^{125}$I-anti-carcinoembryonic Antigen (CEA) Antibodies.

Carcinoembryonic antigen (CEA) is the reference antigen for immunotargeting of gastrointestinal tumors due to an over-expression in almost all colorectal tumors (>95%), a high antigenic density expression (up to 1×10$^6$ CEA molecules per cell) and a very long residence time at the cell surface. However, in radioimmunotherapy (RIT), the non-internalization of CEA rules out the use of low range radio-isotopes such as Auger emitters which are attractive for the treatment of very small tumor nodules. In order to overcome this limitation, DPV15 has been used to induce internalization of the antibody anti-CEA MAb 35A7 (denoted 37A7) and the potential of the conjugate $^{125}$I-35A7-DVP15 has been analyzed for Auger electron therapy.

1) Conjugation:

Conjugation has been carried out following the general plan described example 2. Succinimidyl-4-(N-maleimidomethyl) cyclohexana-1-carbo-xylate (SMCC) has been used to prepare antibody-DPV conjugates containing 3 to 5 peptides molecules per antibody molecule.

```
                                        (SEQ ID NO: 11)
DPV15:  NH2-LRRERQSRLRRERQSR-Cys-COOH
        (Cystein has been added for conjugation).
```

2) In Vitro Studies:

Internalization in LS174T human colon adenocarcinoma cells was analyzed using immunofluorescence microscopy. Cytotoxicity was measured in a clonogenic assay. An irrelevant antibody, PX, was used as control in all the experiments.

Immunofluorescence analysis demonstrated that 35A7-DPV15 conjugate internalized in LS174T cells although native 35A7 did not.

In the clonogenic assay, $^{125}$I-35A7-DVP15 conjugate demonstrated a cytotoxicity. Non-radiolabeled 35A7 and 35A7-DPV15 conjugate as well as $^{125}$I-35A7 did not show any cytotoxicity. The irrelevant conjugate, $^{125}$I-PX-DPV15, exhibited a limited cytotoxicity as compared with $^{125}$I-35A7-

DVP15 demonstrating the need of a specific antibody to eradicate all the LS174T cells.

These in vitro studies demonstrate that the therapeutic effect of $^{125}$I-35A7 is dependent on internalization due to the very short particle range of the Auger electron. $^{125}$I-anti-CEA MAb derived with DPV are potential candidates for Auger electron radioimmunotherapy in digestive cancers.

3) In Vivo Therapeutic Effect Assay of $^{125}$I-35A7-DPV15

3.1) First Study: Single Injection $^{125}$I-35A7-DPV15 has been studied on SWISS nude mice with LS174T tumors compared with NaCl. LS174T tumors have been established by subcutaneous injection 2×10$^6$ by mouse at Day zero. A single dose of $^{125}$I-35A7-DPV15 has been injected by intra-venous (i.v.) route 8 days after cells transplantation. $^{125}$I-35A7-DPV15 has been injected to 0.125 mCi, 0.25 mCi, 0.5 mCi and 1 mCi. Tumour volume, medullar toxicity and mice weight were observed and controlled until 45 days after transplantation.

This first in vivo study showed a slowing down in LS174T tumor growth when using $^{125}$I-35A7-DPV15 compared with NaCl. These results suggest that the effective dose should be superior to 1 mCi. Furthermore, no toxicity has been observed.

3.2) Second Study: Two Injections

In the second study, SWISS nude mice with LS174T tumors have been treated with two injections of $^{125}$I-35A7-DPV15 compared with NaCl. The conjugate has been injected by intra-venous (iv) route 8 and 12 days after cells transplantation. The doses used were 2×NaCl, 2×0.5 mCi and 2×1 mCi. Tumor volume, medullar toxicity and mice weight were observed and controlled until 60 days after transplantation.

Tumor growth has been significantly slowed down by the treatment compared with NaCl. The median survival time is 20 days for the mice in the group treated with NaCl, 30 days for the mice in the group treated with 2×0.5 mCi $^{125}$I-35A7-DPV15 and about 40 days for the mice in the group treated with 2×1 mCi $^{125}$I-35A7-DPV15. Furthermore, no toxicity has been observed.

Example 8

In Vivo Efficacy Studies of DPV15- and DPV15b-Doxorubicin Conjugates

1) Coupling Peptides to Doxorubicin

Doxorubicin, an anti-tumor agent, has been conjugated to DPV15 and DPV15b following the process described in the PCT patent application, publication number WO 04/011033.

DPV15: (SEQ ID NO: 11)
NH2-LRRERQSRLRRERQSR-Cys-COOH

DPV15b: (SEQ ID NO: 14)
NH2-Cys-GAYDLRRRERQSRLRRRERQSR-COOH

A cystein has been added for conjugation.

2) Method

Mice: Athymic (nu/nu) nude mice, female, NMRI-nu (nu/nu)-Nude

Tumor model: HCT116 human colorectal carcinoma (ATCC Number: CCl-247)

Experiment has been performed on tumor-bearing mice. The HCT116 tumors have been established by intradermal injection of 100 μl of the cell suspension (10$^7$ cells/0.1 mL) on the right flank of the mouse.

Drugs were diluted in water (Cooper) for injection (10% of the final volume). After complete dissolution a solution of 0.9% NaCl for injection (Cooper) 0.9% was added. The solutions were filtered on 0.2 μm filter. The concentration of doxorubicin and DPV-doxorubicin were controlled in spectrophotometry with the standard curve of doxorubicin concentration.

First Experiment: DPV15-doxorubicin

The solutions were injected by intra veinous (i.v) route in lateral tail vein at 3.5, 5 and 6.5 μmol/kg for the doxorubicin and 15 μmol/kg for the DPV15-Dox following a Q2D3×3W administration schedule (3 injections a week spaced 2 days apart for 3 weeks).

Second Experiment: DPV15b-doxorubicin

The solutions were injected by iv route in lateral tail vein at 5, 6 and 7 μmol/kg for the doxorubicin and 10 μmol/kg for the DPV15b-Dox conjugate following a Q2D3×3W administration schedule.

2) Results

Figure 35:
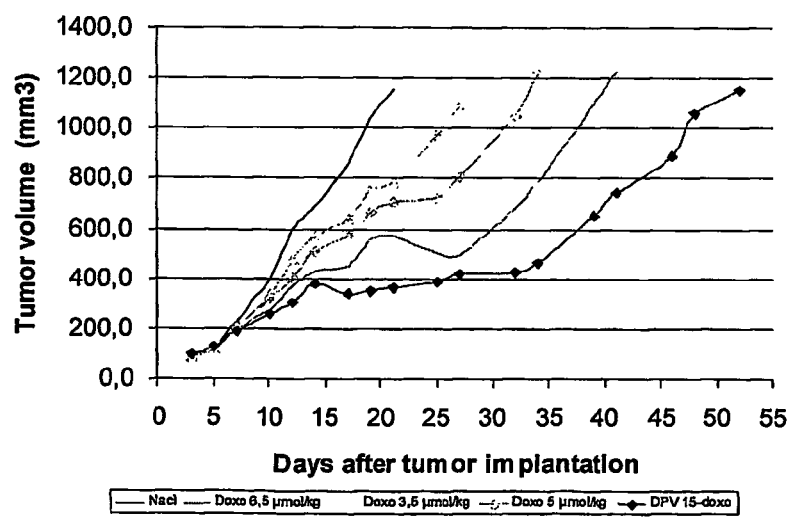
FIG. 35 shows anti-tumor activity of DPV15-doxorubicin conjugate in mice.

First Experiment:

FIG. 35 shows anti-tumor activity of DPV15-doxorubicin conjugate. Tumor volume (mm$^3$) is displayed as a function of time (days) after cell implant.

The following table 13 shows the Tumor growth delays and Tumor doubling times.

TABLE 13

|  | Tumor growth delay (days) | Tumor doubling time (days) |
|---|---|---|
| Control (NaCl) | 16.55 | 6.4 |
| DPV15-doxo: 15 μmol/kg | 43.38 | 11.40 |
| Doxorubicin: 3.5 μmol/kg | 21.20 | 10.20 |
| Doxorubicin: 5 μmol/kg | 26.40 | 14.20 |
| Doxorubicin: 6.5 μmol/kg | 35.29 | 22.90 |

DPV15-doxorubicin showed a greater antitumoral activity than free doxorubicin at 6.5 μmol/kg (the highest tested dose) on this model.

Figure 36:
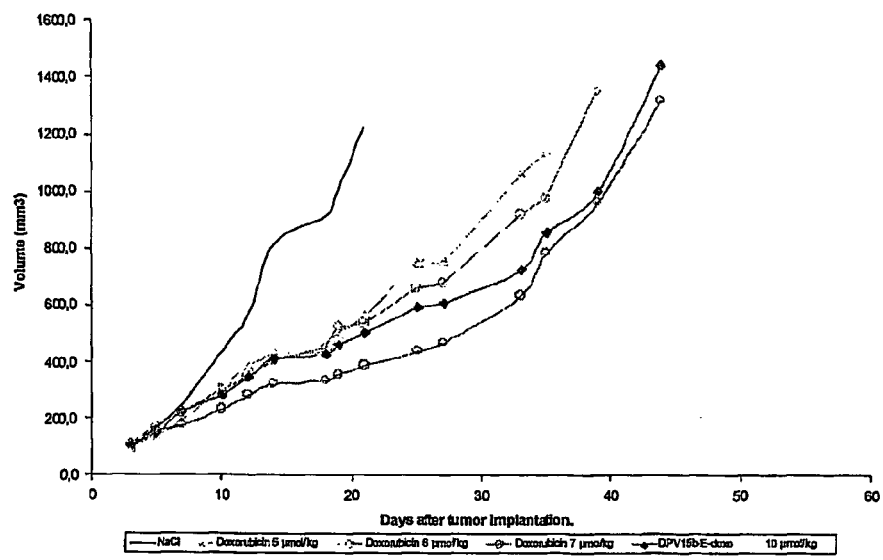
FIG. 36 shows anti-tumor activity of DPV15b-doxorubicin conjugate in mice.

Second Experiment:

FIG. 36 shows anti-tumor activity of DPV15b-doxorubicin conjugate. Tumor volume (mm$^3$) is displayed as a function of time (days) after cell implant. DPV15b-doxorubicin is denoted DPV15b-ε-doxo in the graph.

The following table 14 shows the Tumor growth delays and Tumor doubling times.

TABLE 14

|  | Tumor growth delay (days) | Tumor doubling time (days) |
|---|---|---|
| Control (NaCl) | 13.72 | 4.36 |
| DPV15b-doxo: 10 μmol/kg | 34.17 | 20.82 |
| Doxorubicin: 5 μmol/kg | 27.86 | 15.38 |
| Doxorubicin: 6 μmol/kg | 29.98 | 16.24 |
| Doxorubicin: 7 μmol/kg | 35.16 | 13.38 |

DPV15b-doxorubicin at 10 μmol/kg showed a greater antitumoral activity than free doxorubicin at 6 μmol/kg (higher than doxorubicin MTD on this model), and it showed lower activity than free doxorubicin at 7 μmol/kg. However, the doxorubicin at this dose (7 μmol/kg) exhibited important toxicity (mice body weight loss superior than 20% and neurotoxicity signs).

3) Conclusion

The conjugation of doxorubicin with DPV15 or DPV15b induces a decrease of the doxorubicin toxicity and allows to increase its antitumoral activity.

Example 9

In Vivo Evaluation of the Anti-tumor Activity of DPV7b-doxorubicin Conjugate

1) Coupling Peptides to Doxorubicin

Doxorubicin has been conjugated to DPV7b according to the process described in the PCT patent application, publication number WO 04/011033.

DPV7b:                              (SEQ ID NO: 15)
NH2-GKRKKKGKLGKKRPRSR-Cys-COOH
(Cystein has been added for conjugation)

2) In Vivo Evaluation

Method

Nude mice are injected with $10^7$ HCT116 cells (HCT116 human colorectal carcinoma cell line) intradermically in the right flank. Treatments were performed on established solid tumors (tumors size is about 80 to 90 mm$^3$) at Day 3. Mice were randomized in different groups (equivalent tumors size), 6 mice by group. Three group of mice are treated (Injection, 200 µl/mice (20 g) with Micro-fine +, U-100 insulin 0.5 ml, 0.33×12.7 mm/29G1/2: Becton Dickinson), control group (NaCl), treated group (DPV7b-doxorubicin: 15 µmol/kg) and treated control group (doxorubicin: 3.5, 5 and 6.5 µmol/kg).

Injections are performed by i.v. (intravenous) route in the tail vein at D3 (Day 3), D5, D7, D10, D12, D14, D17, D19, D21 (Q2D3×3W administration schedule).

Weight and tumors size of mice are controlled, on injection days and every 3-4 days after treatment, end of experiment (day 52).

Figure 37:
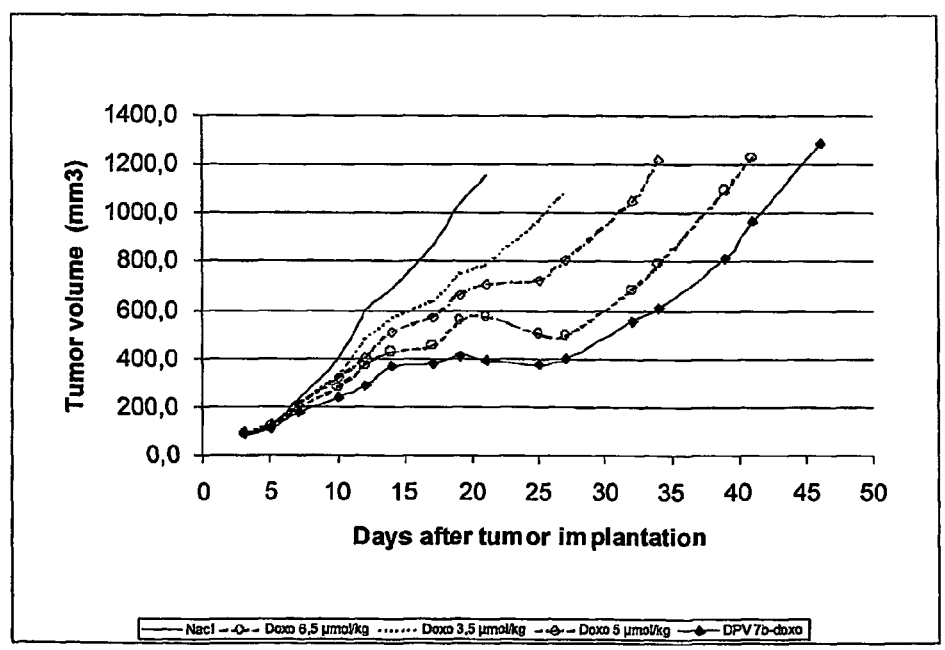
FIG. 37 shows anti-tumor activity of DPV7b-doxorubicin conjugate in mice.

Results:

FIG. 37 shows anti-tumor activity of DPV7b-doxorubicin conjugate. Tumor volume (mm$^3$) is displayed as a function of time (days) after cell implant The following table 15 shows the Tumor growth delays and Tumor doubling times.

TABLE 15

|  | Tumor growth delay (days) | Tumor doubling time (days) |
|---|---|---|
| Control (NaCl) | 16.55 | 6.4 |
| DPV7b-doxo: 15 µmol/kg | 39.00 | 12.2 |
| Doxorubicin: 3.5 µmol/kg | 21.20 | 10.2 |
| Doxorubicin: 5 µmol/kg | 26.40 | 14.6 |
| Doxorubicin: 6.5 µmol/kg | 35.29 | 22.9 |

DPV7b-doxorubicin conjugate shows an in vivo antitumor efficacy on HCT116 tumor.

Example 10

In Vivo Evaluation of the Anti-tumor Activity of DPV3-RNAse A Conjugate

RNAse A (Ribonuclease A) exhibits a molecular mass of 14.4 kDa.

1) Coupling Peptides to Ribonuclease A

Conjugate DPV3-RNAse was prepared following the general plan (see Example 1).

DPV3:                              (SEQ ID NO: 12)
NH2-RKKRRRESRKKRRRES-Cys-COOH
(Cystein has been added for conjugation)

2) In Vivo Evaluation

Method

NMri Nude mice are injected with HCT116 human colorectal carcinoma cells intradermically in the right flank.

Mice were treated by peri-tumoral injection of a solution of $H_2O$/NaCl (v/v: 1/9), RNAse (100 µg, 0.5 mg/ml) and DPV3-RNAse (100 µg, 0.5 mg/ml), following a Q2D3×2W administration schedule.

Results

Figure 38:
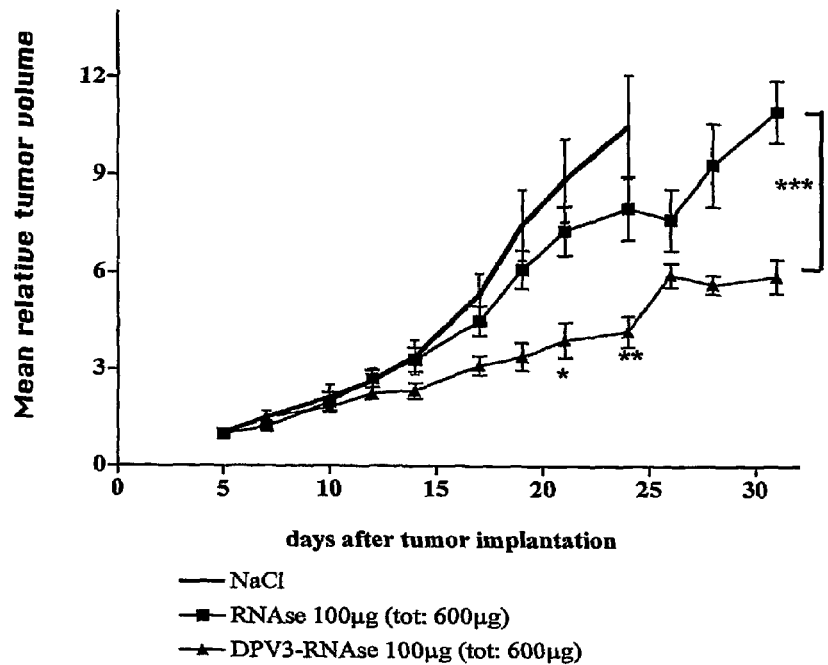
FIG. 38 shows anti-tumor activity of DPV3-RNAse A conjugate in mice.

Results are shown in FIG. 38: Tumor volume (mm$^3$) is displayed as a function of time (days) after cell implant.

Administration of 600 µg of DPV3-RNAse A over a period of two weeks reduces tumor growth when compared to RNAse A only.

Example 11

In Vitro Comparative Internalizations of DPV-Peroxidase Conjugates (DPV-PO)

Peroxidase (PO) was chosen to represent the capacity of the DPVs to internalize medium size proteins (40 000 Da). The use of a preactivated form of the protein allows the preparation of homogenous conjugates (only 1 DPV per PO molecule). Penetration of DPV-PO conjugates was tested in both HCT116 (colorectal carcinoma) and HeLa (cervix adenocarcinoma) cell lines.

Protocol of conjugation and internalization has been carried out according to Example 1.

DPV Compared:

DPV3:                              (SEQ ID NO: 12)
NH2-RKKRRRESRKKRRRESC-COOH

DPV3/10:                           (SEQ ID NO: 16)
NH2-RKKRRRESRRARRSPRHLC-COOH

DPV6:                              (SEQ ID NO: 17)
NH2-GRPRESGKKRKRKRLKPC-COOH

DPV7:                              (SEQ ID NO: 18)
NH2-GKRKKKGKLGKKRDPC-COOH

DPV7b:                             (SEQ ID NO: 15)
NH2-GKRKKKGKLGKKRPRSRC-COOH

DPV10:                             (SEQ ID NO: 19)
NH2-SRRARRSPRHLGSGC-COOH

DPV10/6:                           (SEQ ID NO: 20)
NH2-SRRARRSPRESGKKRKRKRC-COOH

Respectively SEQ ID No 4, 5, 6, 8, 9, 3, 7 with a C-terminal Cystein.

Results

Figure 39:
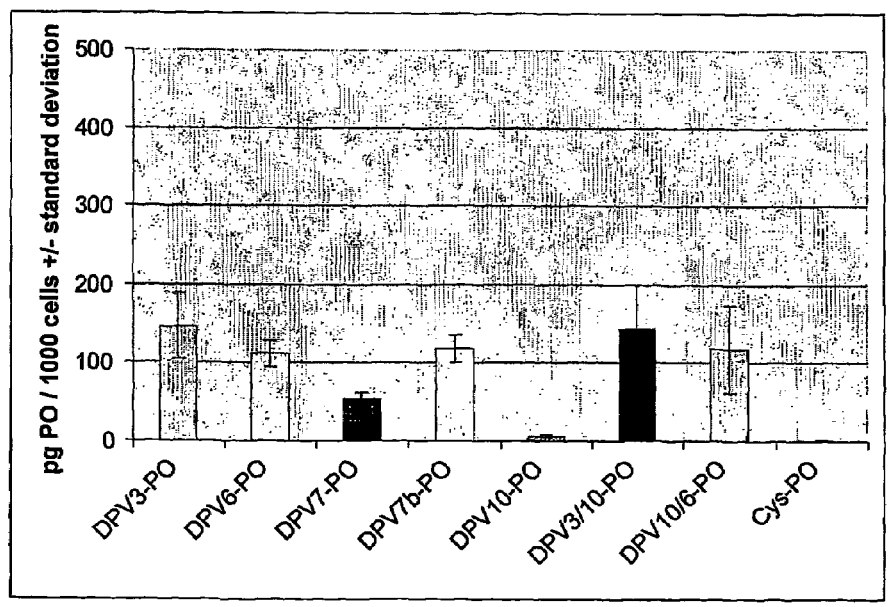
FIG. 39 shows quantitative penetration of the DPVs 3, 6, 7, 7b, 10, 3/10 and 10/6-PO conjugates in HCT116 cells.

Quantitative penetration of the DPV-PO conjugates in HCT116 cells is represented FIG. 39. Cell lysis was performed after 4 hours of incubation at an initial DPV-PO conjugates concentration of 75 µg/ml (corresponding to approximately 1.8 µM). Results are given as the mean value obtained in three independent experiments, all realized in duplicates.

The following table 16 shows net quantities of DPV-PO conjugates internalized in HCT116 cells. Results are given in picograms PO/1000 cells.

TABLE 16

| Conjugates | pg PO/1000 cells | Standard deviation |
| --- | --- | --- |
| DPV3-PO | 147 | 41 |
| DPV6-PO | 111 | 18 |
| DPV7-PO | 54 | 7 |
| DPV7b-PO | 118 | 17 |
| DPV10-PO | 6 | 2 |
| DPV3/10-PO | 143 | 56 |
| DPV10/6-PO | 117 | 56 |
| Cys-PO | 1 | 1 |

Figure 40:
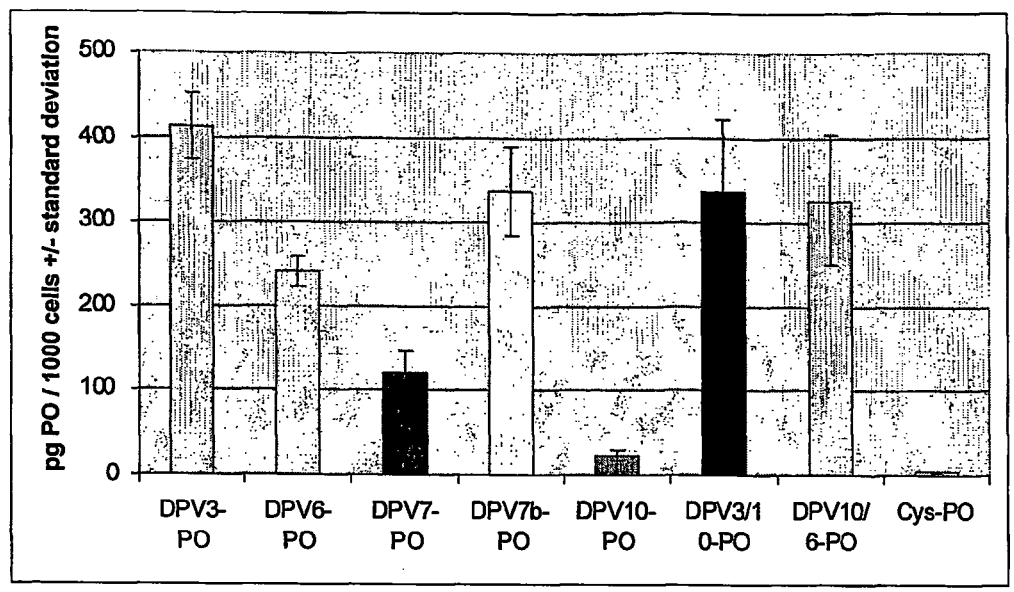
FIG. 40 shows quantitative penetration of the DPVs 3, 6, 7, 7b, 10, 3/10 and 10/6-PO conjugates in HeLa cells.

Quantitative penetration of the DPV-PO conjugates in HeLa cells is represented FIG. 40. Cells were incubated for 4 hours in the presence of the conjugates at an initial concentration of 75 µg/ml. Results are given as the mean value obtained in three independent experiments, all realized in duplicates.

The following table 17 shows net quantities of DPV-PO conjugates internalized in HeLa cells. Results are given in picograms/1000 cells.

TABLE 17

| Conjugates | pg PO/1000 cells | Standard deviation |
| --- | --- | --- |
| DPV3-PO | 413 | 38 |
| DPV6-PO | 241 | 19 |
| DPV7-PO | 122 | 26 |
| DPV7b-PO | 337 | 53 |
| DPV10-PO | 24 | 5 |
| DPV3/10-PO | 338 | 84 |
| DPV10/6-PO | 327 | 78 |
| Cys-PO | 4 | 2 |

The following table 18 discloses the cell localization and the intracellular accumulation level of the DPV-PO conjugates.

TABLE 18

| Conjugates | Predominant localization | Intracellular accumulation level |
| --- | --- | --- |
| DPV10-PO | nuclear | low |
| DPV7-PO | cytoplasmic | Medium |
| DPV3-PO | cytoplasmic | HIGH |
| DPV6-PO | cytoplasmic | HIGH |
| DPV7b-PO | cytoplasmic | HIGH |
| DPV3/10-PO | cytoplasmic | HIGH |
| DPV10/6-PO | cytoplasmic | HIGH |

The level of DPV-PO intracellular accumulation is variable, as a function of the DPV, and as a function of the cell line (always higher in HeLa cells). The general repartition of the DPVs is nevertheless mainly identical in the two observed cell lines, with three main groups of high, medium and low intracellular accumulation. It is important to notice that the level of intracellular accumulation of the "nuclear" DPVs (DPV10) is much lower than that of the "cytoplasmic" DPVs (DPV3, 6 and 7).

Example 12

In Vitro Comparative Intracellular Accumulation in Adherent Cells of DPV-AntiPO IgG Anti-Peroxidase Immunoglobulin (AntiPO-IgG or aPO) was chosen to represent the capacity of the DPVs to internalize very high molecular weight proteins (150 000 Da). Internalization experiments were realized in both HCT116 (colorectal carcinoma) and HeLa (cervical adenocarcinoma) cell lines. Intracellular accumulation was evaluated at a single time point (4 hours).

Protocol of conjugation and internalization has been carried out according to Example 2.

DPV amino acid sequences used and compared are those described in Example 11.

Figure 41:
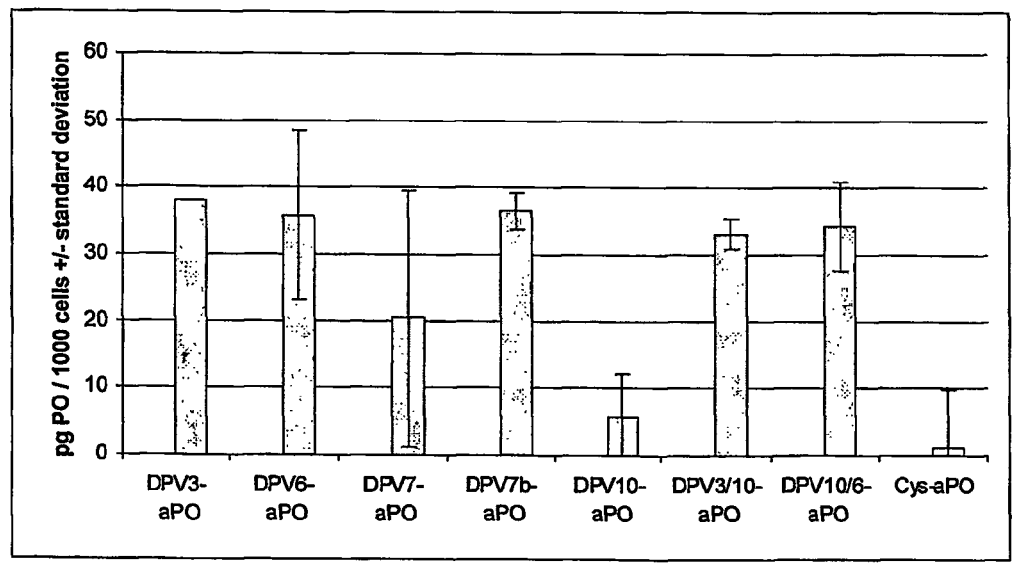
FIG. 41 shows quantitative penetration of the DPVs 3, 6, 7, 7b, 10, 3/10 and 10/6-antiPO IgG conjugates in HCT116 cells.

Results:

Quantitative penetration of the DPV-antiPO IgG conjugates in HCT116 cells is represented FIG. 41. Cells were incubated for 4 hours in the presence of the conjugates at an initial concentration of 100 µg/ml. Results are given as the mean value obtained in three independent experiments, all realized in duplicates.

The following table 19 shows quantities of DPV-antiPO IgG conjugates (denoted DPV-aPo) internalized in HCT116 cells. Results are given in picograms PO/1000 cells, as the mean of three independent experiments.

TABLE 19

| Conjugates | pg PO/1000 cells | Standard deviation |
| --- | --- | --- |
| DPV3-aPO | 38.1 | 12.8 |
| DPV6-aPO | 35.8 | 19.2 |
| DPV7-aPO | 20.4 | 2.8 |
| DPV7b-aPO | 36.5 | 6.3 |
| DPV10-aPO | 5.8 | 2.3 |
| DPV3/10-aPO | 33.3 | 6.7 |
| DPV10/6-aPO | 34.4 | 8.7 |
| Cys-aPO | 1.1 | 0.9 |

Figure 42:
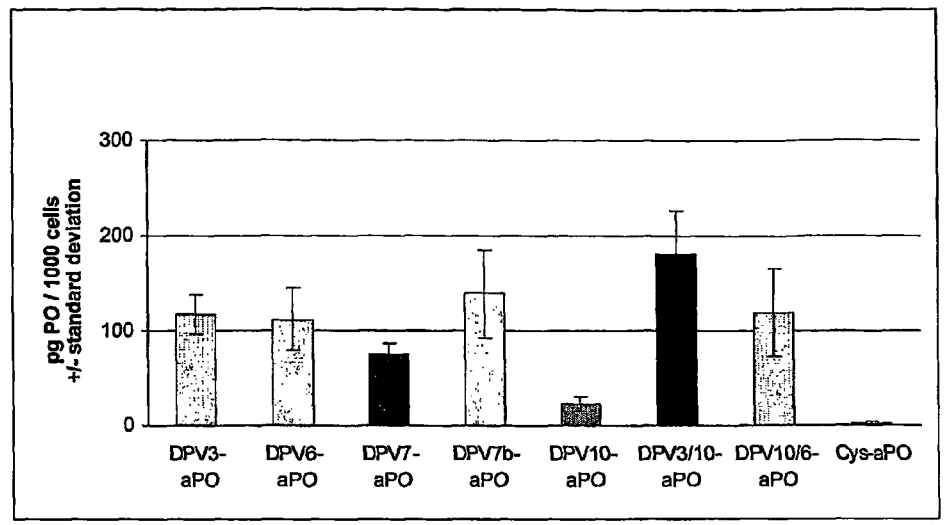
FIG. 42 shows quantitative penetration of the DPVs 3, 6, 7, 7b, 10, 3/10 and 10/6-antiPO IgG conjugates in HeLa cells.
Figure 43:
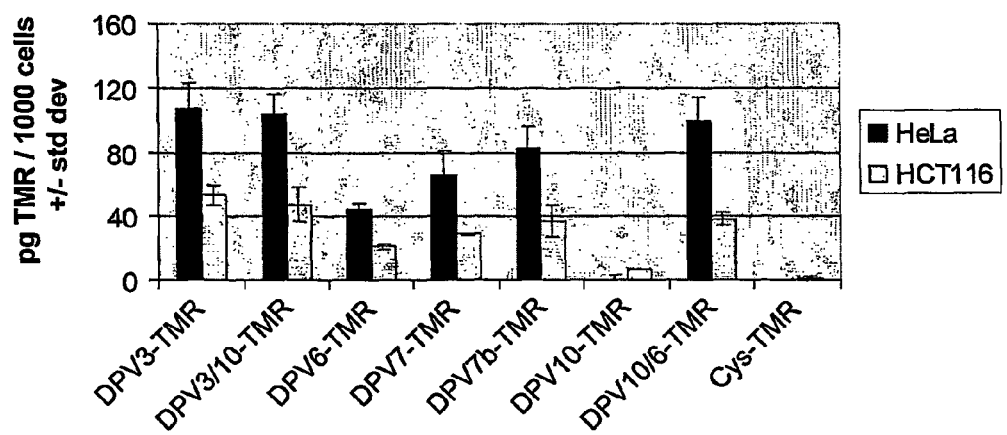
FIG. 43 shows the level of internalisation of the DPVs 3, 6, 7, 7b, 10, 3/10 and 10/6-TMR conjugates in HeLa and HCT116 cells.

Quantitative penetration of the DPV-antiPO IgG conjugates in HeLa cells is represented FIG. 42. Cells were incubated for 4 hours in the presence of the conjugates at an initial concentration of 100 µg/ml. Results are given as the mean value obtained in three independent experiments, all realized in duplicates.

The following table 20 shows net quantities of DPV-antiPO conjugates internalized in HeLa cells. Results are given as the mean value of three independent experiments, in picograms PO/1000 cells.

TABLE 20

| Conjugates | pg PO/1000 cells | Standard deviation |
| --- | --- | --- |
| DPV3-aPO | 117.0 | 21.2 |
| DPV6-aPO | 111.9 | 33.5 |
| DPV7-aPO | 75.3 | 12.4 |
| DPV7b-aPO | 138.7 | 45.6 |
| DPV10-aPO | 23.0 | 7.6 |
| DPV3/10-aPO | 181.0 | 45.6 |
| DPV10/6-aPO | 119.4 | 46.4 |
| Cys-aPO | 1.7 | 2.2 |

The following table 21 discloses the cell localization and the intracellular accumulation level of the DPV-AntiPO conjugates.

TABLE 21

| Conjugates | Predominant localization | Intracellular accumulation level |
| --- | --- | --- |
| DPV10-PO | nuclear | low |
| DPV7-PO | cytoplasmic | Medium |
| DPV3-PO | cytoplasmic | HIGH |
| DPV6-PO | cytoplasmic | HIGH |
| DPV7b-PO | cytoplasmic | HIGH |

TABLE 21-continued

| Conjugates | Predominant localization | Intracellular accumulation level |
|---|---|---|
| DPV3/10-PO | cytoplasmic | HIGH |
| DPV10/6-PO | cytoplasmic | HIGH |

The level of internalization of the DPV-IgG conjugates is different in the two cell lines tested. Intracellular accumulation is always stronger in HeLa cells. Moreover, the classification of conjugates in three groups considering their level of intracellular accumulation also leads to the exact same repartition of DPVs whatever of those two is conjugated (either PO or immunoglobulin).

Example 13

In Vitro Comparative Internalizations of DPV-TMR Conjugates (TMR: Tetramethylrhodamine-5-maleimide)

Penetration of DPV-TMR conjugates was tested in both HCT116 (colorectal carcinoma) and HeLa (cervix adenocarcinoma) cell lines.

Protocol of conjugation and internalization has been carried out according to Example 3.

DPV amino acid sequences used and compared are those described in Example 11.

Results

Level of internalisation of DPV-TMR conjugates in HeLa and HCT116 cells is represented FIG. 43.

After accumulation of DPV-TMR conjugates for two hours at 37° C., cells were trypsinized, lysed, and fluorescence was quantified in the cell lysates. Results are the mean of at least 4 values.

The following table 22 shows levels of DPV-TMR conjugates internalization. Values are given in pg TMR/1000 cells in HeLa and HCT116 cells after 2 hours internalization at 37° C., at an initial concentration of 20 μM of conjugate.

TABLE 22

| | pg TMR/1000 cells | |
|---|---|---|
| Conjugates | HeLa | HCT116 |
| DPV10-TMR | 0.00 | 6.78 |
| DPV6-TMR | 44.21 | 20.90 |
| DPV7-TMR | 65.90 | 28.61 |
| DPV3-TMR | 107.74 | 53.18 |
| DPV7b-TMR | 82.82 | 36.67 |
| DPV3/10-TMR | 103.91 | 47.53 |
| DPV10/6-TMR | 99.23 | 38.57 |
| Cys-TMR | 0.00 | 0.91 |

As seen in FIG. 43 and Table 22, there are important differences in the level of internalization of the various DPV-TMR conjugates, depending on both the conjugate, and the cell line. Nevertheless, as was previously observed for DPV-PO and DPV-IgG conjugates, the classification of the DPVs as a function of the quantity of internalized TMR is similar in both cell lines and is as follows: DPV3≧DPV3/10≧DPV 10/6≧DPV7b>DPV7>DPV6>DPV10.

The invention claimed is:

1. An amino acid sequence comrprising Leu Arg Arg Glu Arg Gln Ser Arg Leu Arg Arg Glu Arg Gln Ser Arg (SEQ ID NO:1) or Gly Ala Tyr Asp Leu Arg Arg Arg Glu Arg Gln Ser Arg Leu Arg Arg Arg Glu Arg Gln Ser Arg (SEQ ID NO:2).

2. A combination of an amino acid sequence according to claim 1 wherein a substance of interest is conjugated to SEQ ID NO:1 or SEQ ID NO:2.

3. A method of preparing a composition for the transfer of a substance of interest into cells, comprising combining the amino acid sequence of claim 1 with a substance of interest to produce the said composition.

4. A biological, pharmaceutical, cosmetic, agro-food, diagnostic or tracking composition, comprising as active ingredient an amino acid sequence according to claim 1.

* * * * *